US011344733B2

(12) United States Patent
Kaiser et al.

(10) Patent No.: US 11,344,733 B2
(45) Date of Patent: May 31, 2022

(54) APPARATUS, SYSTEMS, AND METHODS TO IMPROVE ATRIAL FIBRILLATION OUTCOMES INVOLVING THE LEFT ATRIAL APPENDAGE

(71) Applicant: APBLATION INNOVATIONS, LLC, Brentwood, TN (US)

(72) Inventors: Daniel Walter Kaiser, Nashville, TN (US); Robert A. Pickett, Nashville, TN (US); Katie Miyashiro, Portland, OR (US); Clayton A. Kaiser, Nashville, TN (US)

(73) Assignee: ABLATION INNOVATIONS, LLC, Brentwood, TN (US)

( * ) Notice: Subject to any disclaimer, the term of this patent is extended or adjusted under 35 U.S.C. 154(b) by 0 days.

(21) Appl. No.: 17/227,183

(22) Filed: Apr. 9, 2021

(65) Prior Publication Data

US 2021/0260391 A1    Aug. 26, 2021

Related U.S. Application Data

(63) Continuation of application No. 16/796,895, filed on Feb. 20, 2020.

(60) Provisional application No. 62/808,130, filed on Feb. 20, 2019.

(51) Int. Cl.
| | | |
|---|---|---|
| *A61N 1/372* | (2006.01) | |
| *A61N 1/375* | (2006.01) | |
| *A61B 17/12* | (2006.01) | |
| *A61B 18/00* | (2006.01) | |

(52) U.S. Cl.
CPC .... *A61N 1/37512* (2017.08); *A61B 17/12031* (2013.01); *A61B 17/12122* (2013.01); *A61N 1/3756* (2013.01); *A61N 1/37211* (2013.01); *A61B 2018/00577* (2013.01)

(58) Field of Classification Search
CPC ............ A61N 1/37512; A61N 1/39622; A61N 1/362; A61N 1/06; A61N 1/3968; A61B 17/12122; A61B 2017/00243; A61B 2018/1475; A61B 2018/1495; A61B 5/7275
See application file for complete search history.

(56) References Cited

U.S. PATENT DOCUMENTS

| | | | | |
|---|---|---|---|---|
| 2003/0120337 | A1* | 6/2003 | Van Tassel | A61B 17/12172 623/1.23 |
| 2016/0158561 | A1* | 6/2016 | Reddy | A61N 1/362 607/32 |
| 2020/0155863 | A1* | 5/2020 | Min | A61N 1/3622 |

* cited by examiner

*Primary Examiner* — Jon Eric C Morales
(74) *Attorney, Agent, or Firm* — Vista IP Law Group LLP; William A. English

(57) ABSTRACT

Apparatus, systems, and methods are provided for monitoring AF episodes, delivering ATP pulses, and/or achieving electrical isolation of the left atrial appendage (LAA) of a patient's heart and/or preventing thrombus formation after electrical isolation. For example, devices are provided that may implanted from within the left atrium, e.g., to isolate the LAA, prevent thrombus formation within the LAA, facilitate endothelialization, and/or deliver pacing.

25 Claims, 34 Drawing Sheets

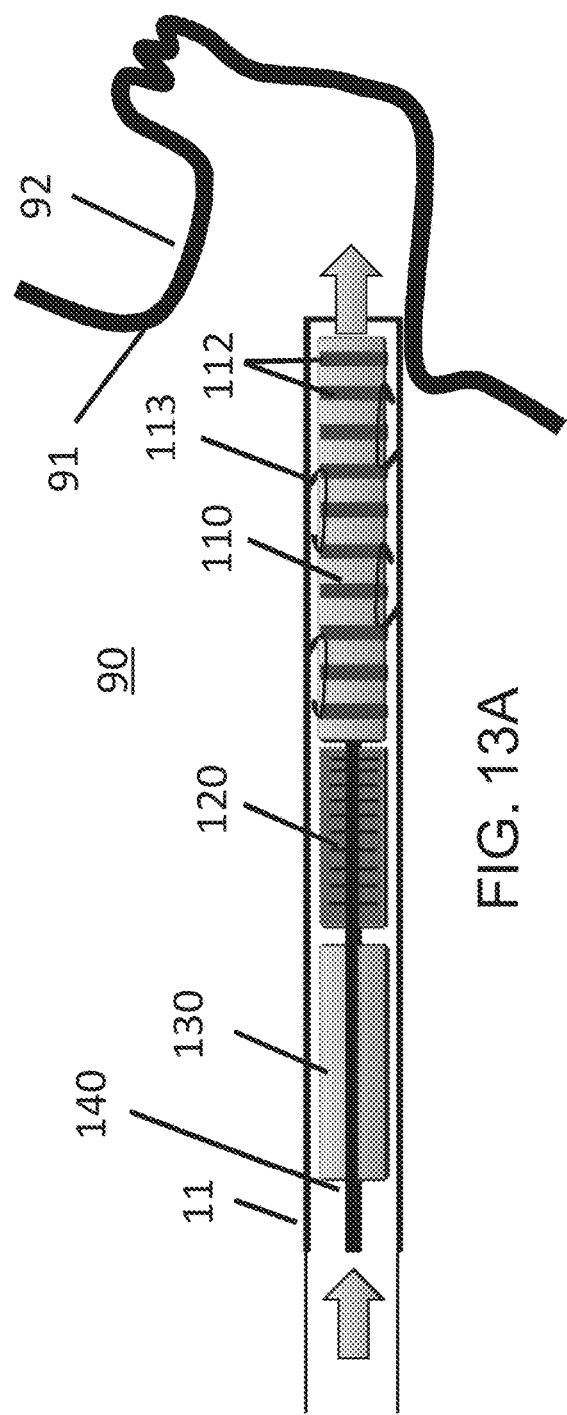
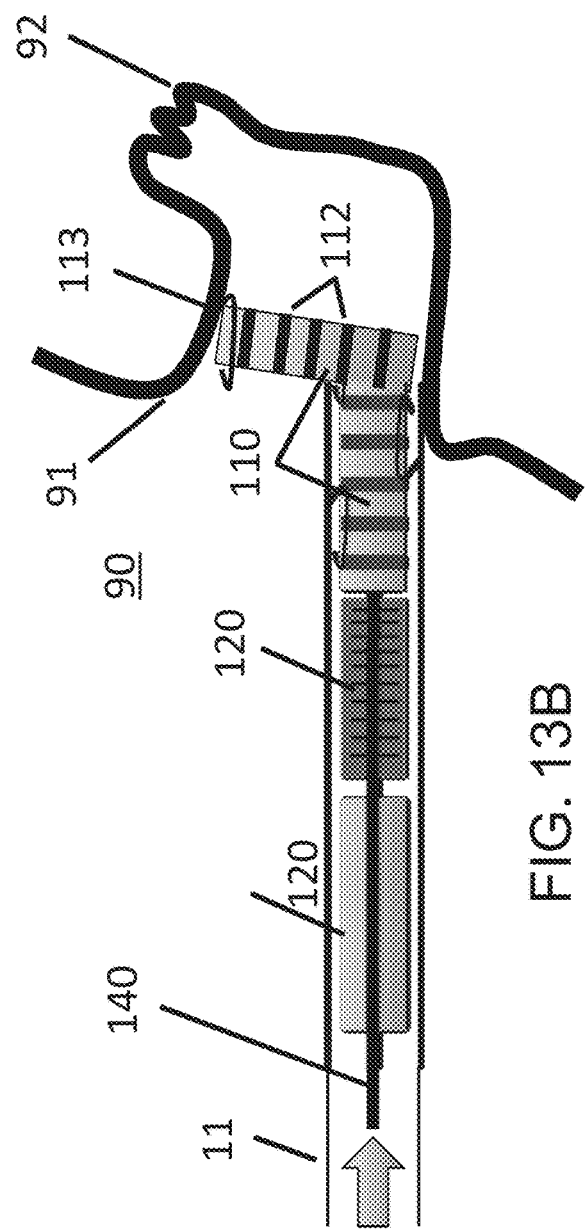

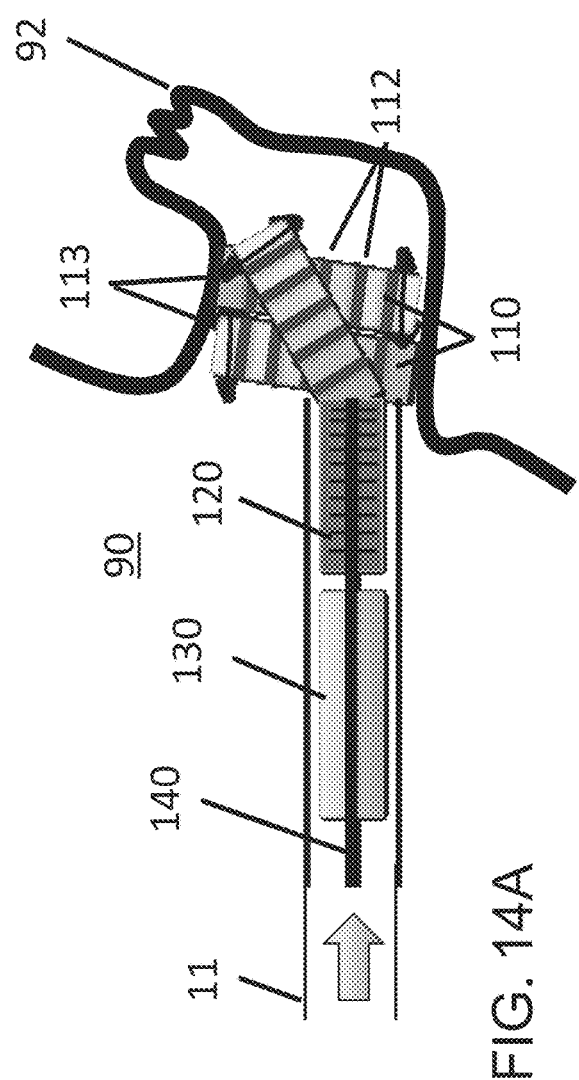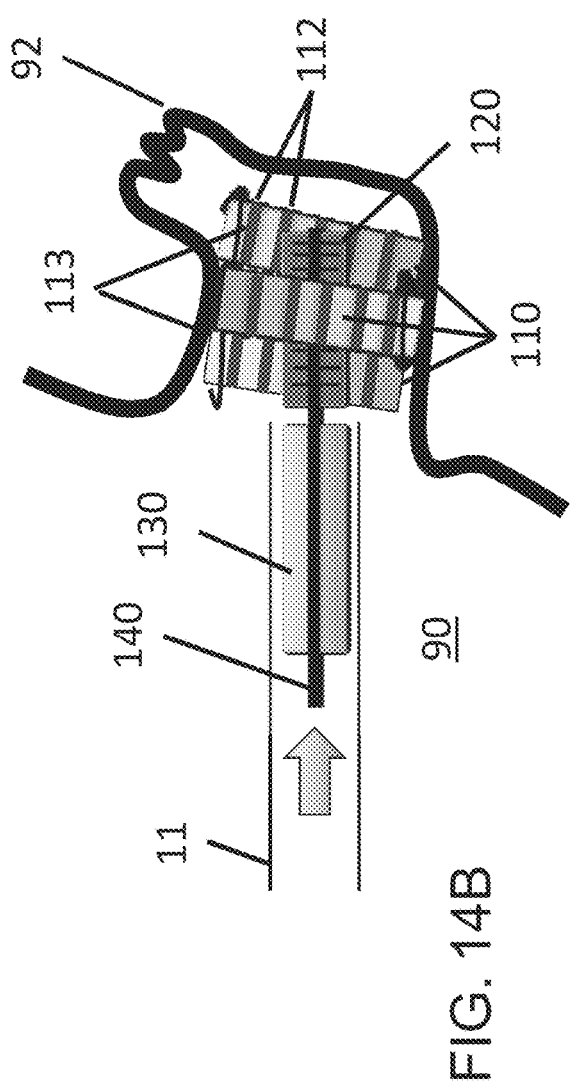

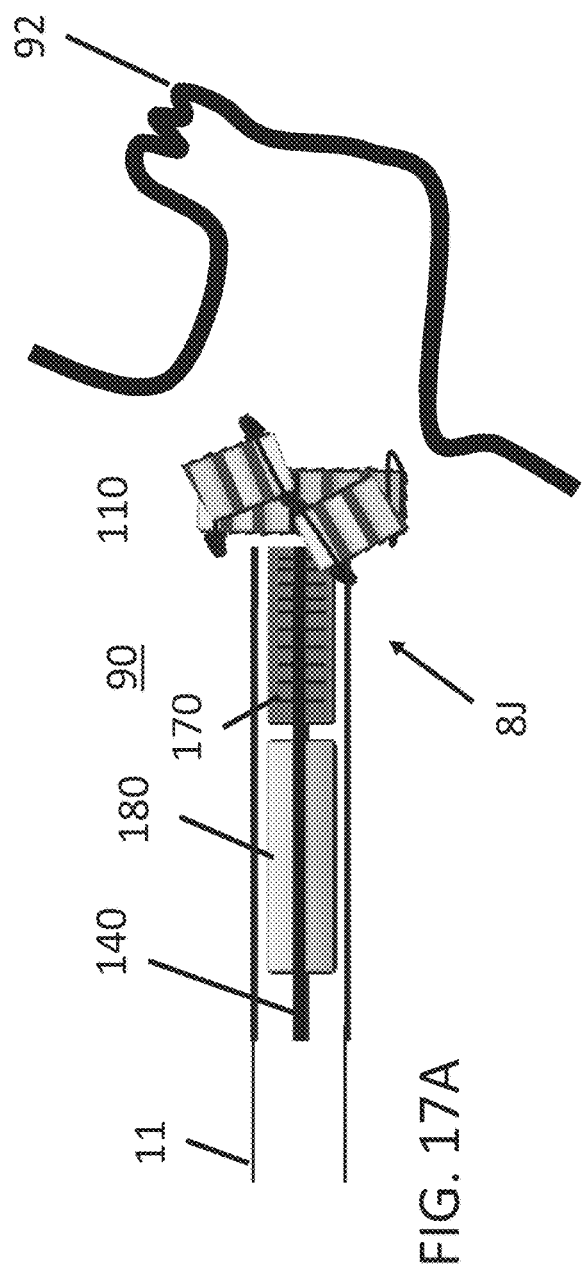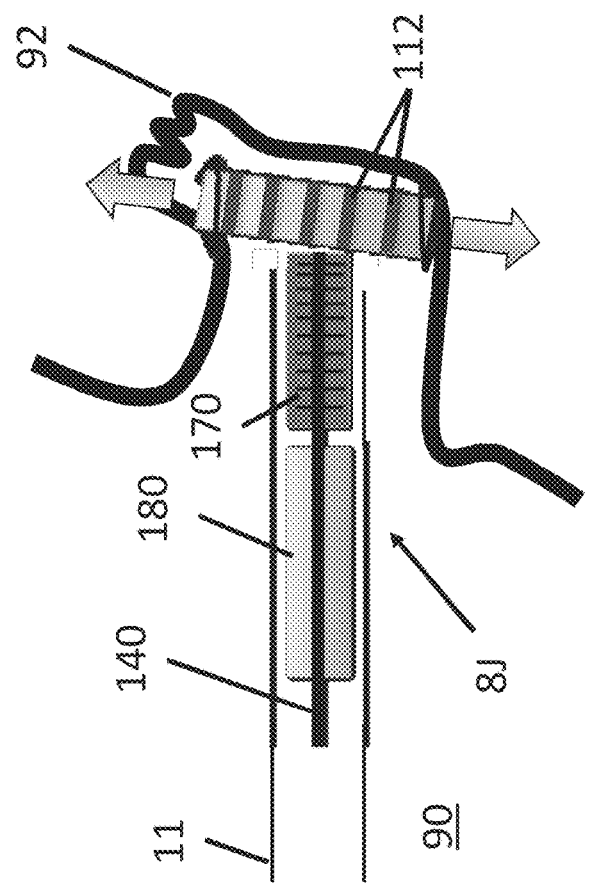
FIG. 17A
FIG. 17B

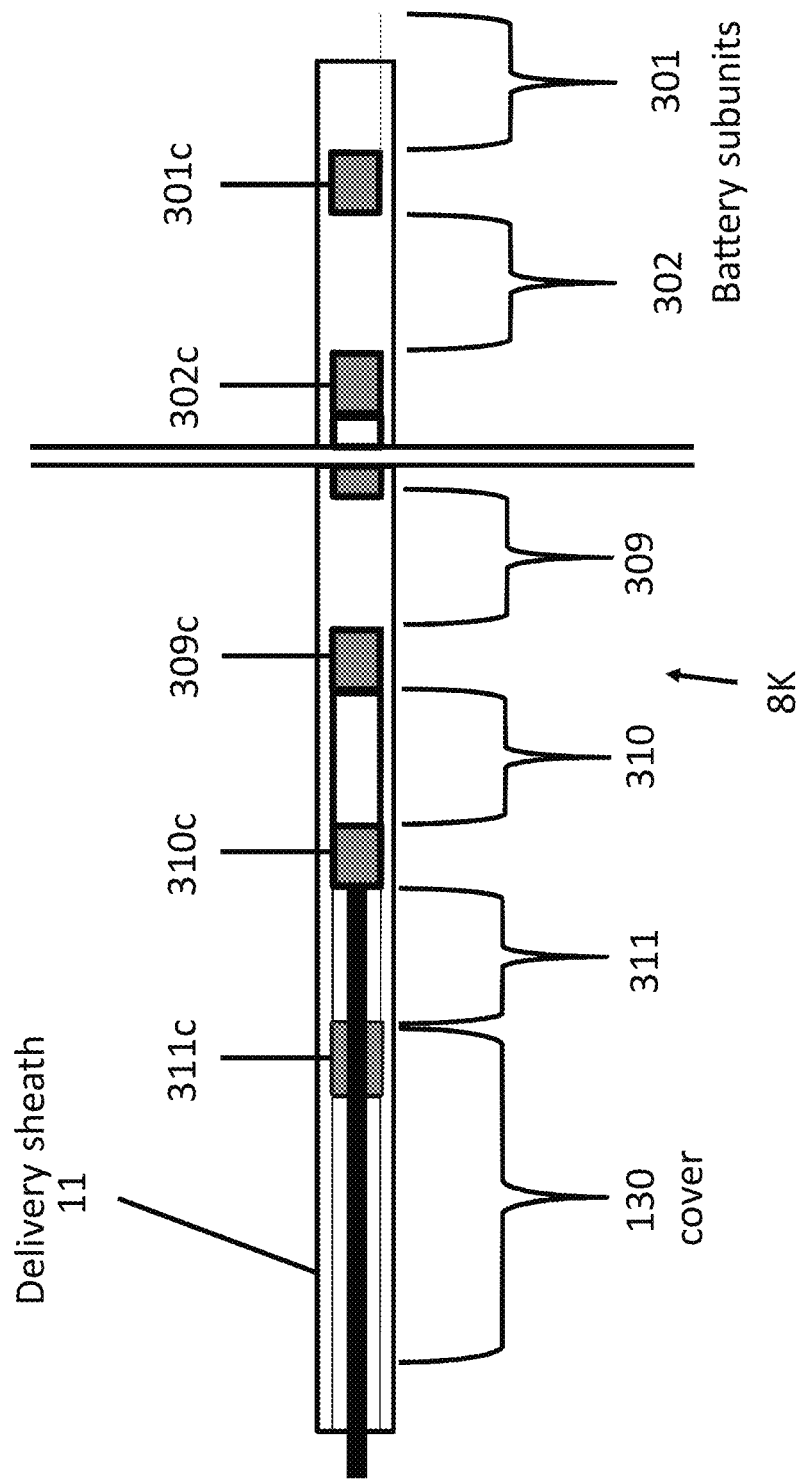

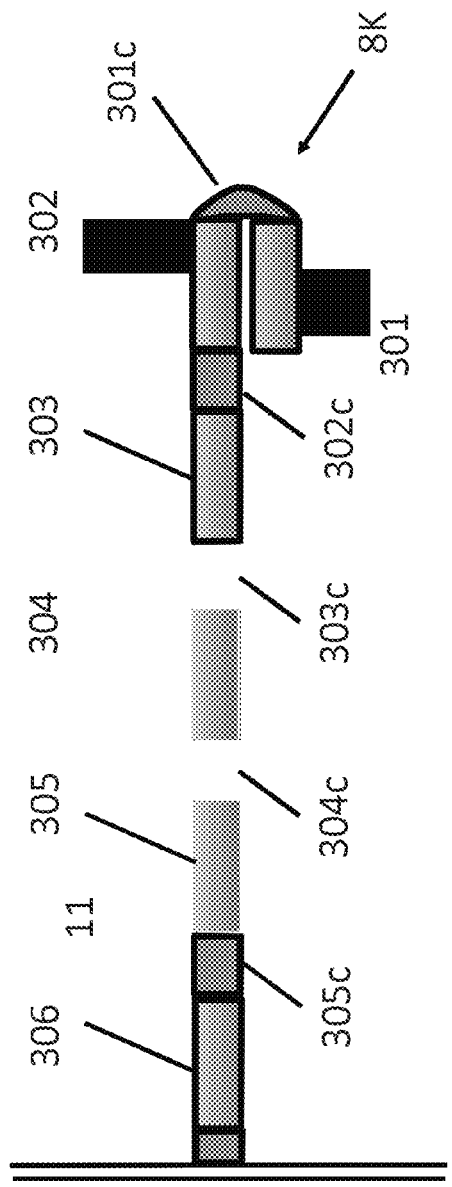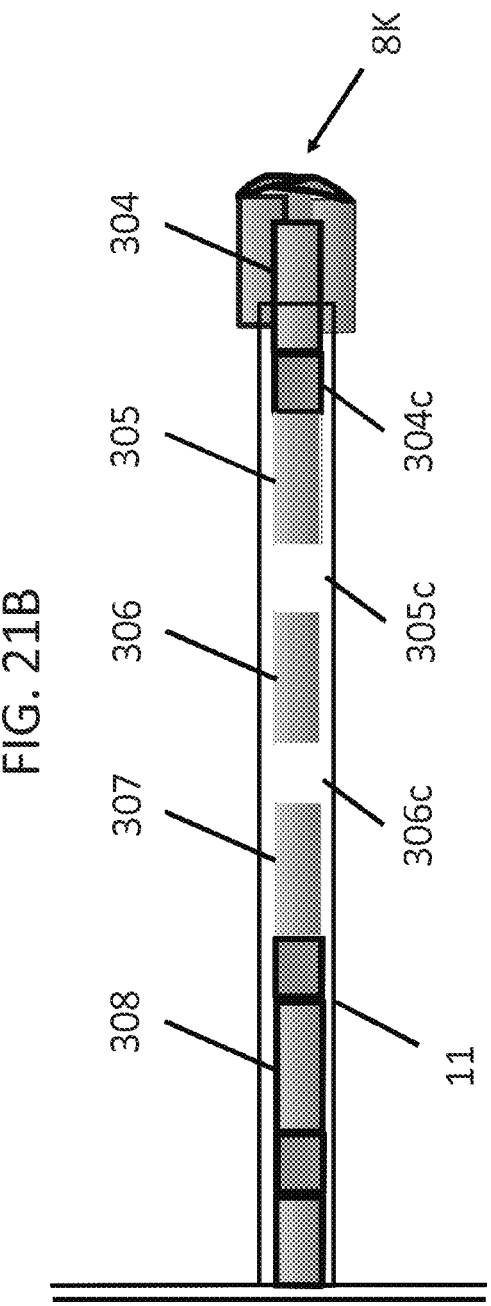

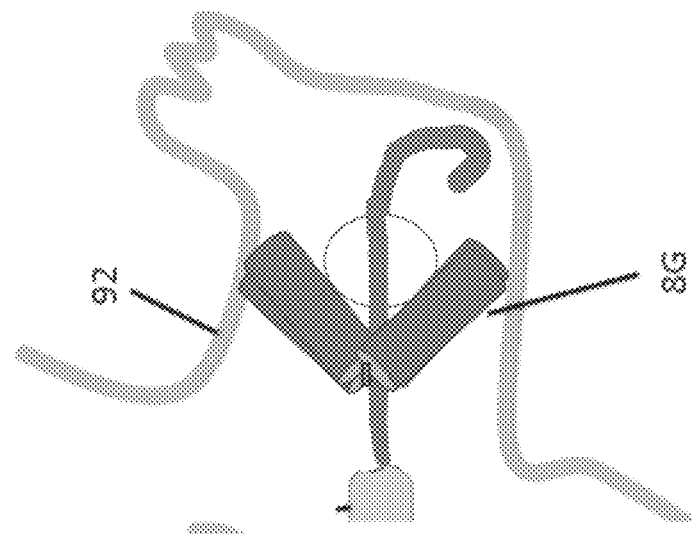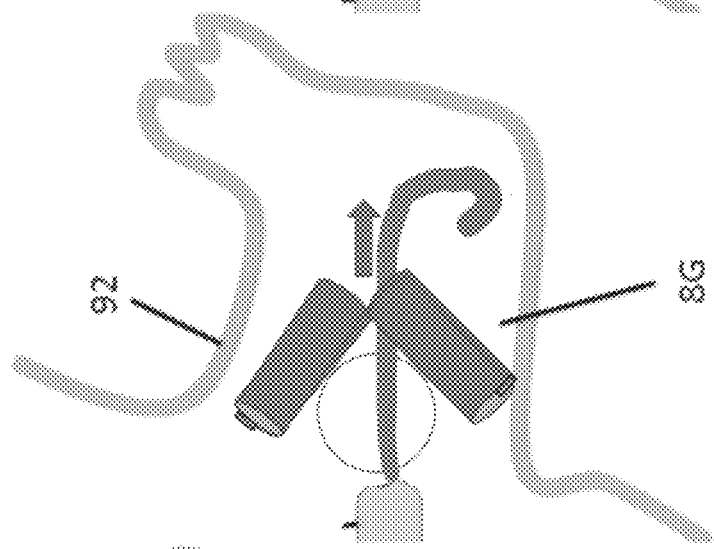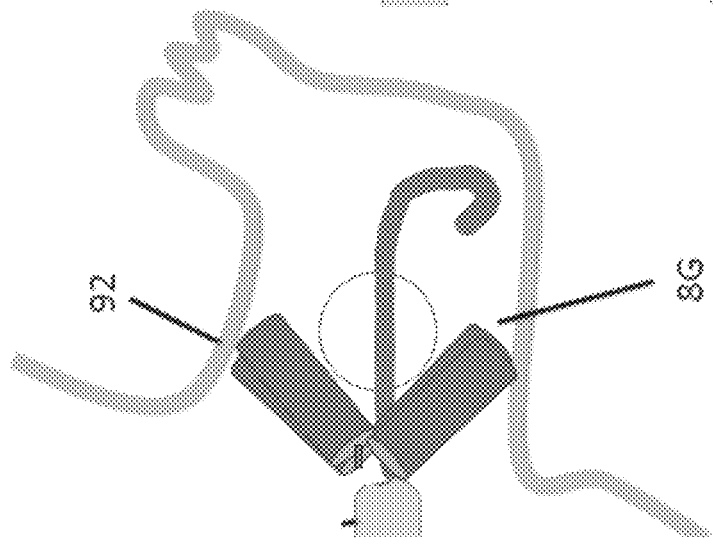

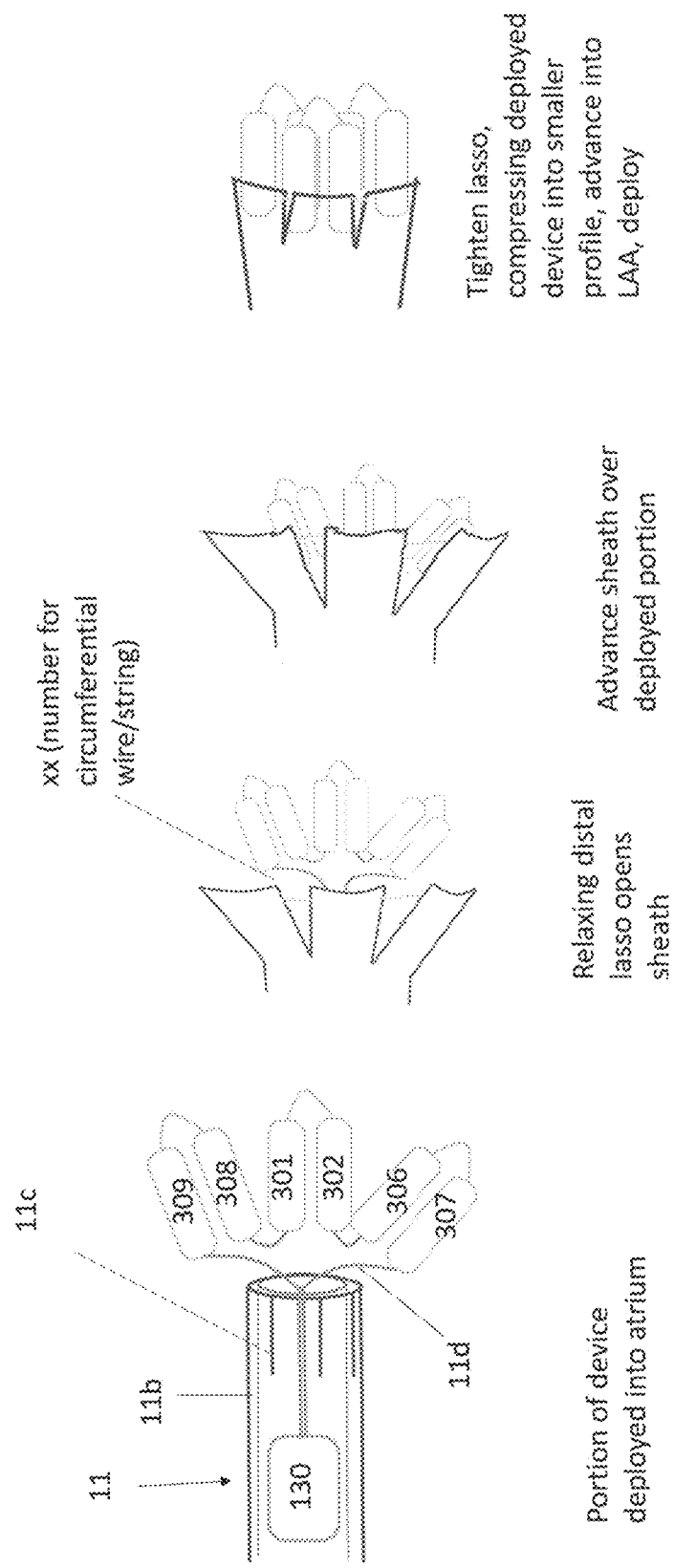

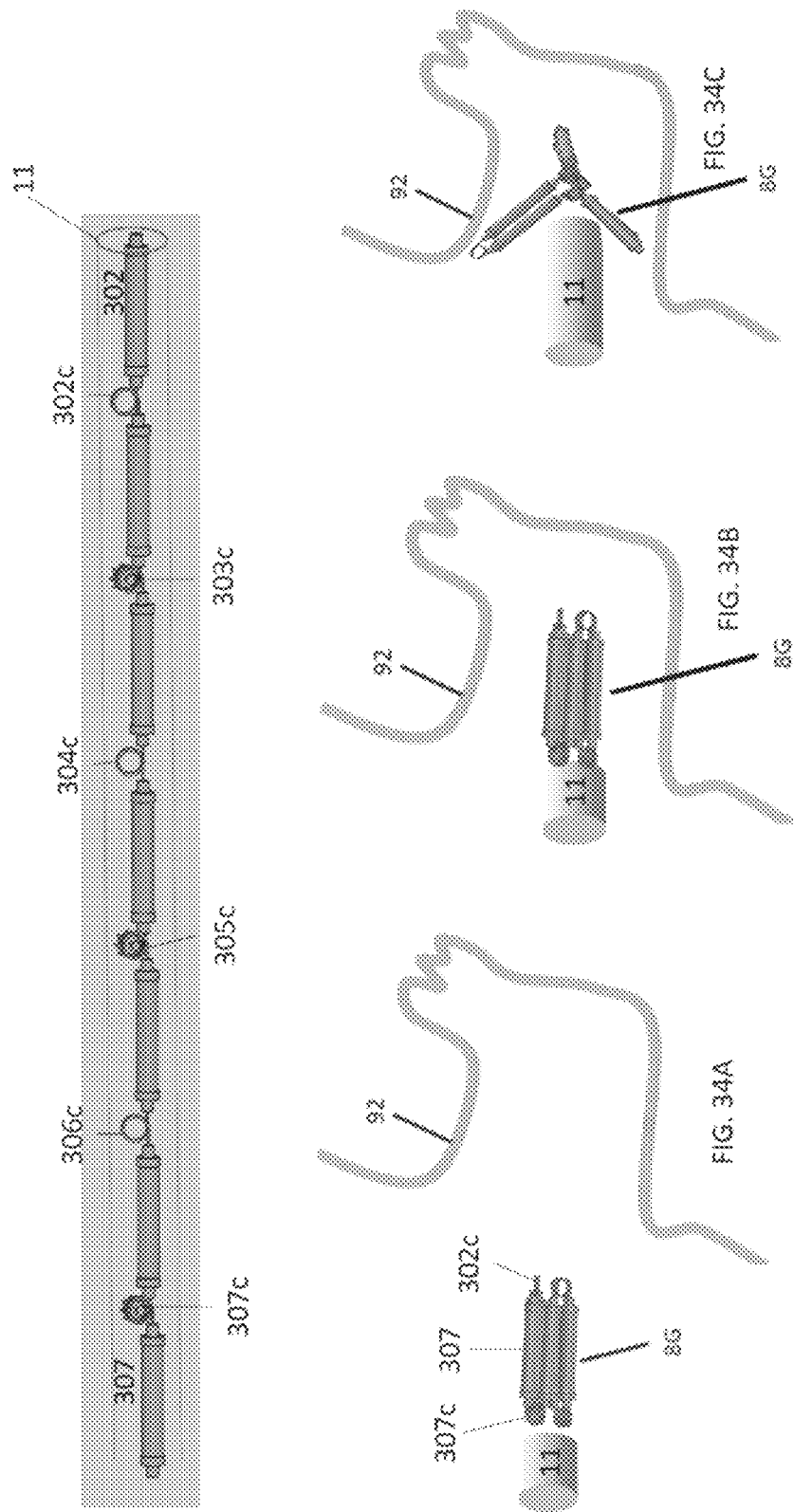

APPARATUS, SYSTEMS, AND METHODS TO IMPROVE ATRIAL FIBRILLATION OUTCOMES INVOLVING THE LEFT ATRIAL APPENDAGE

RELATED APPLICATION DATA

The present application is a continuation of co-pending application Ser. No. 16/796,895, filed Feb. 20, 2020, which claims benefit of provisional application Ser. No. 62/808,130, filed Feb. 20, 2019, the entire disclosures of which are expressly incorporated by reference herein.

FIELD OF THE INVENTION

The present invention relates to apparatus, systems, and methods for improving atrial fibrillation outcomes involving the left atrial appendage. More specifically, implantable devices are provided that are designed for placement within a patient's body, e.g., within the left atrial appendage of the atrium of a patient's heart to monitor and treat abnormal rhythms.

BACKGROUND

Atrial fibrillation ("AF") is the most common sustained cardiac arrhythmias. Cardiac ablation of atrial fibrillation is one of most common cardiac procedures. The cornerstone of AF ablation procedures have been pulmonary vein isolation ("PVI"). However, in recent years, non-pulmonary vein triggers have been identified. One of the most common non-pulmonary vein triggers is the left atrial appendage ("LAA"). Therefore, there is a growing interest in performing LAA isolation during ablation procedures. However, there are technical difficulties in creating electrical isolation of the LAA. In addition, numerous reports suggest that there is increased risk of thromboembolic events following LAA isolation. Inadequate function of the LAA after electrical isolation is felt to be responsible. After electrical isolation, the LAA does not squeeze adequately. As a result, blood can coagulate to form a thrombus in the LAA. This thrombus can then embolize to other parts of the body.

The LAA has various morphologies and sizes. An ablation tool needs to be adaptive enough to accommodate these differences. Some LAA have a straight structure ('windsock' morphology) while other LAA morphologies include a sharp bend ('chicken-wing' morphology). In addition, an ablation tool that prevents thrombus formation within the LAA is optimal. There are data that suggest that some patients who are in sinus rhythm remain at risk for thrombus formation in the LAA after electrical isolation of the LAA.

The only commercially available leadless pacemaker is intended to be placed in the right ventricle. There are apparently next generation leadless pacemakers under development to enable placement within the right atrium. However, there are no known devices available or in development that describes a leadless pacemaker designed to be placed within the left atrium.

Therefore, improved tools to improve AF ablation procedures, e.g., by monitoring AF episodes, delivering ATP pulses, and/or isolating the LAA without the increased risk of thromboembolic events, may be useful.

SUMMARY

The present invention relates to apparatus, systems, and methods for monitoring AF episodes, delivering ATP pulses, and/or achieving electrical isolation of the left atrial appendage (LAA) of a patient's heart and/or preventing thrombus formation after electrical isolation.

More particularly, the systems and methods herein may include a device that is implanted from within the left atrium, isolates the LAA, and prevents thrombus formation within the LAA. In addition, the device may include material that facilitates endothelialization. In an exemplary embodiment, the device may be placed within the body through a sheath and takes a desired shape after leaving the deployment sheath.

Anti-tachycardia pacing (ATP) delivered from traditional pacemakers has been shown to reduce atrial fibrillation burden. It is likely that a leadless pacemaker implanted within the left atrial appendage can also deliver ATP pulses to terminate atrial arrhythmias. A pacemaker in the left atrial appendage can reduce AF burden and prevent thrombus from forming in the left atrial appendage.

In general, patients who go into AF need to be on blood thinners to prevent thrombus formation. A medical device placed into the LAA may help prevent thrombus from forming inside the LAA. In addition, the LAA also provides potential space for a processor and battery. In addition, this space may be used for monitoring purposes. This enables the device to monitor for AF recurrence and alert patients and/or their caretakers. In addition, if the implanted device is able to deliver anti-tachycardia pacing (ATP) pulses to the atrial tissue, the device may help pace-terminate AF episodes if the ablation/isolation procedure is unsuccessful. In addition, patients with AF often demonstrate both fast heart rates (tachycardia) as well as slow heart rates (bradycardia). The device may pace the heart in response to slow heart rates to treat these abnormal rhythms.

Most AF triggers or initiators originate from the left atrium. Specifically, the large majority of atrial tachycardia episodes that initiate and sustain AF episodes come from the pulmonary veins (which connect to the left atrial) and the left atrial appendage. These atrial tachycardia episodes can be interrupted and terminated via anti-tachycardia pacing (ATP). However, ATP episodes are more effective if the ATP pulses are in proximity to the originator of the atrial tachycardia. Therefore, delivering ATP pulses from the left atrium is likely to be more effective than ATP delivery from the right atrium.

Anti-tachycardia pacing (ATP) may be delivered from an implantable pacemaker implanted within the left atrial appendage to terminate atrial tachycardia and atrial flutter. By terminating regular rhythms, a pacemaker in the left atrial appendage may reduce AF burden and prevent thrombus from forming in the left atrial appendage.

In accordance with one embodiment, the LAA isolating device is aligned with electrodes. These electrodes may enable the device to be visualized on mapping systems. This enables mapping systems that use impedance-based mapping or magnetically-based mapping to be visualized to help deploy the device optimally into the LAA. In some embodiments, the device may also include materials to enhance visualization using other methods, such as echocardiography and fluoroscopy, to further aid optimal deployment and placement into the LAA.

In addition, the system may include a monitor of the patient's rhythm. In one embodiment, after the device is deployed and the LAA is isolated, the system is still able to sense and pace the heart. In one embodiment, the device may pace the heart in order to terminate abnormal rhythms. In another embodiment, the device may identify atrial fibrillation and send messages outside of the body. In order to record and send transmissions, in some embodiments, the device may include a battery and/or other implanted power source. In some embodiments, the battery may be charged from the outside world, e.g., inductively, using ultrasound, electromagnetic energy, or otherwise using an external device that communicates with the implanted device.

In accordance with another embodiment, the system may include an elongate member that is designed to be deployed through a specialized deployment sheath into the left atrial appendage. The device coils on itself to fill, attach, and then close off the left atrial appendage from the rest of the left atrium. In addition, electrodes may align the elongate member. These electrodes permit deployment using standard mapping systems (e.g., using impedance or magnetic based systems) as well as ablation to electrically isolate the left atrial appendage. In other embodiments, the device may use electroporation and laser ablation to ablate tissue. In other embodiments, the device may be cooled to freeze LAA tissue to isolate the appendage. In addition, the device may provide a radial force to compress the tissue to induce electrical isolation.

The elongate member may be designed to coil on itself. In addition or alternatively, an inner cable or the like, the materials of the coil itself, or positioning from the delivery system may be utilized to enlarge the coil to optimize contact and force. In other embodiments, electrodes are used to help guide the closure device into place and are then withdrawn. In another embodiment, many or all of the electrodes are deployed and left within the left atrium and/or left atrial appendage.

In some embodiments, detailed imaging is performed on the left atrium and left atrial appendage to better determine the anatomy to facilitate electrical isolation and device deployment. Imaging may be obtained using normal mapping electrodes used during the ablation procedure, or using catheters and electrodes specifically designed to map the LA and LAA. In another embodiment, ultrasound imaging, such as obtained from a transesophageal echocardiogram ("TEE") images or intracardiac echocardiogram images are combined with other mapping techniques to best understand the LAA anatomy. For example, an intracardiac echocardiography ("ICE") catheter may be advanced into the LAA to determine the anatomy. The walls and anatomy of the LAA may be visualized and identified on ultrasound imaging and then incorporated into a three-dimensional map to determine optimal ablation device size/length as well as device deployment within the LAA. A specialized tip may be placed on the tip of the ICE catheter to prevent traumatic damage to the LAA.

In another embodiment, the isolation device combines aspects of an LAA closure device. In one embodiment, electrodes are used to guide device deployment which combines self-expanding nitinol with electrodes for positioning and electrical isolation. In another embodiment, a sponge-like material is used to occlude the LAA. By leading the sponge-like material with electrodes, the sponge-like material may be optimally deployed within the LAA. The sponge-like material may then help lock the electrodes in place and decrease the risk of device embolization.

In another embodiment, after detailed mapping is created, the sponge-like material is cut to optimally fit within the LAA. For example, a desired mass or section of sponge-like material may be formed using a 3D printing system. In one embodiment, the LAA closure material is printed using a specially-designed 3D printer. In another embodiment, the sponge-like material is trimmed to fit the LAA anatomy. In this embodiment, the 3D printer only carves the outside of the sponge-like material—it does not lay down the material. The sponge-like material can then be collapsed to fit within a delivery sheath and deployed within the LAA. The sponge-like material may be aligned with electrodes. In another embodiment, there are electrodes leading the sponge-like material, behind the sponge-like material, located between the beginning and end of the sponge-like material, or a combination thereof.

In another embodiment, two sheaths are used to electrically isolate and then close the LAA. In this embodiment, one sheath is used to map the LAA and facilitate safe deployment of the second sheath into the LAA.

In exemplary embodiments, electrical isolation may occur through pinching or clamping tissue of the LAA. The closure device may be coated with insulation material to force electrical current to optimize tissue ablation.

The connection between the electrodes on the closure device and the external world need to be cut or released at some point. This connection may be rotated to release (a screw mechanism), pulled into the delivery sheath to release, or may be designed to break away with force. In another embodiment, electrical current is used to burn or electrolytically separate the connection to facilitate release.

In another embodiment, the closure device is used to deliver a chemical that prevents the body from healing the ablation. In one embodiment, the device is covered with chemotherapy agents that prevent electrical reconnection. Therefore, the electrodes may deliver RF or electrical current to induce electroporation ablation to the LAA. The device may combine electroporation, chemical ablation, and pressure to maintain electrical isolation. The device may also contain distal electrodes capable of sensing distal LAA electrical signals in order to verify electrical isolation. The closure device may include a battery to maintain electrical ablation. In addition, the closure device may include a communication system to communicate outside of the body. In one embodiment, the closure device can be charged from outside the body using ultrasound energy. The device may then use this energy to measure left atrial pressure or pace the heart.

In response sinus slow heart rates such as bradycardia or sinus arrest, the devices herein may be configured to pace the atrium to speed up the heart rate. However, pacing the LAA after electrical isolation may not increase the heart rate since the LAA will be electrically isolated from the rest of the heart. Therefore, the device needs to be implanted within the LAA to prevent thrombus formation; however, the electrodes need to have contact to atrial tissue outside of the LAA in order to affect the heart rate. Therefore, in an alternatively embodiment, the device may be configured to be positioned within the LAA but has electrodes adjacent atrial tissue outside the LAA in order to pace heart tissue to speed up the heart rate.

Furthermore, AF is often initiated by fast and sometimes irregular heart rhythms such as atrial flutter or atrial tachycardia. By deliver pacing pulses at a rate faster than the sensed atrial rate, overdrive pacing is often able to terminate the abnormal atrial rhythm. Therefore, delivering ATP from the device can help terminate tachyarrhythmias. In addition, even though the device is positioned in the left atrial appendage, this location is often overhanging the left ventricle. Therefore, by delivering high output pacing, the device may be designed to treat abnormally slow ventricular rates in the setting of poor atrio-ventricular conduction, such as heart block.

In addition, the closure device may be covered in drug eluting material that prevents the body from healing the lesion. In one embodiment, the closure device delivers an agent that prevents electrical reconnection; this agent may include one or more of sirolimus, paclitaxel, zotarolimus, everolimus, biolinx polymer, a steroid, and ridaforolimus material. In addition or alternatively, the device may include a steroid eluting agent. In another embodiment, the closure device is designed to facilitate endothelialization, including containing endothelial progenitor cell capture material, basic polymeric woven or non-woven materials, or surfaces roughened through mechanical or chemical methods. In another embodiment, the closure device is covered with radioactive material that facilitates electrical isolation.

Other aspects and features including the need for and use of the present invention will become apparent from consideration of the following description taken in conjunction with the accompanying drawings.

BRIEF DESCRIPTION OF THE DRAWINGS

FIGS. 13A-16B show an exemplary method for delivering the device of FIG. 10.

FIGS. 17A-19B show an exemplary method for delivering another leadless pacemaker into the left atrial appendage.

FIG. 20 is a schematic illustration of yet another embodiment of a leadless pacemaker designed for deployment into or near a left atrial appendage.

FIG. 21A-26 shows an exemplary method for deploying the device of FIG. 20.

FIGS. 30A-30C are cross-sectional views of a region of a heart showing another embodiment of a leadless pacemaker device being deployed within the left atrial appendage of a heart.

FIGS. 31A-31D show an exemplary method for manipulating a leadless pacemaker device for introduction into a left atrial appendage of a heart.

FIG. 33 is a side view of still another example of a leadless pacemaker device.

FIGS. 34A-34C are cross-sectional views of a region of a heart showing a method for deploying the device of FIG. 33 within the left atrial appendage of a heart.

DETAILED DESCRIPTION OF THE EXEMPLARY EMBODIMENTS

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 1:
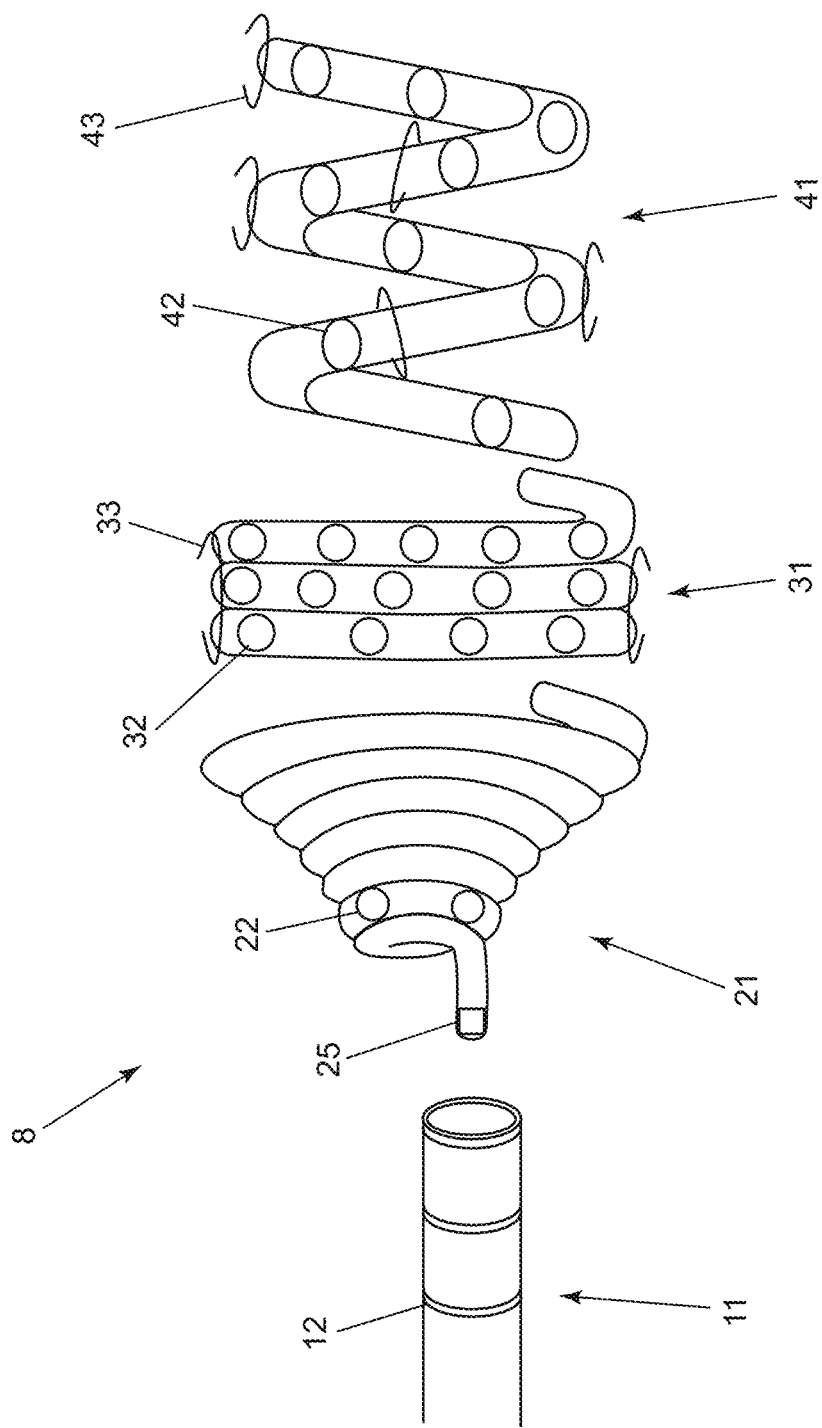
FIG. 1 is a side view of an exemplary embodiment of a leadless pacemaker device designed for implantation within the left atrial appendage that includes three portions deployed from a distal portion of a delivery sheath.

Turning to the drawings, FIG. 1 shows an exemplary embodiment of an ablation device 8 for electrical isolation of a left atrial appendage ("LAA"). In this example, the ablation device 8 includes three components, segments, or portions that are introduced, deployed, and remain within the vicinity of the LAA: an occluding portion 21, an ablation/compression portion 31, and an anchoring portion 41. The components of the device 8 may be introduced and/or deployed using a deployment sheath or other tubular and/or elongate member 11. The components may be separate devices that may be deployed sequentially or they may be components of a single integral device including different regions. In the embodiment shown, the deployment sheath 11 includes one or more electrodes 12 (two shown) on its distal end to facilitate positioning the components of the device 8. In some embodiments, the distal end of the sheath 11 may be biased to a predetermined shape, e.g., including a bend or curve to facilitate the components of the device 8 being deployed from the deployment sheath 11 in a controlled method.

The occluding portion 21 may also be lined by or otherwise include a plurality of electrodes 22. The occluding portion 21 may be a self-expanding disc to close off the LAA from the rest of the left atrium ("LA") of a subject's heart. In another embodiment, the occluding portion 21 is biased to a predetermined helical and/or conical shape, e.g., that spirals on itself like a pyramid, that may be shaped to completely close off the LAA when deployed. Optionally, the occluding portion 21 may be made of or covered in certain material that facilitates endothelialization and/or minimizes platelet aggregation.

The ablation/compression portion 31 is designed to be enlarged at the ostium of the LAA to electrically isolate the LAA. The ablation/compression portion 31 may be lined by and/or otherwise include electrodes 32 that may be monitored and/or identified, e.g., using an external imaging and/or mapping system (not shown). In addition, the ablation/compression portion 31 includes one or more electrodes 32, e.g., a plurality of spaced-apart electrodes as shown, which may be used to deliver radiofrequency energy, electroporation, freezing temperature, or force to the tissue at the LAA ostium to electrically isolate the LAA from the rest of the LA. The ablation/compression portion 31 may also include one or more tines or other fixturing elements 33 to prevent device movement and/or embolization of the device 8 after deployment. The ablation/compression portion 31 may have an inner cable or plunger (not shown) that enables the portion 31 to be enlarged after deployment to optimize radially force and tissue contact.

With continued reference to FIG. 1, the anchoring portion 41 may also include one or more anchoring portion electrodes 42, e.g., a plurality of spaced-apart electrodes as shown, to help position the anchoring portion 41 within the LAA. The anchoring portion 41 may also include a plurality of anchoring portion tines or other fixturing elements 43 spaced apart along the anchoring portion 41 to help anchor the device 8 within the LAA to prevent movement and/or embolization of the device 8.

In addition, the device 8 may also include an electrical connector 25, e.g., for detachably coupling one or more components of the device 8 to an elongate deliver member (not shown). For example, as shown in FIG. 1, an electrical connector 25 may be included on a proximal end of the occluding portion 21, although, in addition or alternatively, an electrical connector may also be included on the ablation/compression portion 31, or even the anchoring portion 41 (not shown). The electrical connector 25 includes one or more electrical connections, e.g., coupled to one or more wires or electrical leads (not shown) between the electrodes 22, 32, 42 on the device components and a controller and/or other devices external to the patient (not shown) to facilitate device positioning and ablation of cardiac tissue.

Optionally, the electrical connector 25 may have a specialized cover (not shown) that once the connection is decoupled, the electrical components are covered to prevent exposure within the heart. For example, the electrical connector 25 may be part of the ablation/compression segment 31, such that after the electrical connections are decoupled, the electrical connections will not have access to blood within the LA by the occluding portion 21.

In another embodiment, the occluding portion electrodes 22 may be used to measure impedance across the occluding section 21, e.g., to monitor for complete coverage of the LAA ostium. In one embodiment, the impedance between the occluding portion electrodes 22 may be used as a surrogate for comprehensive contact between loops of the pyramid shape to identify if there are any gaps in the occluding portion 21.

Figure 2:
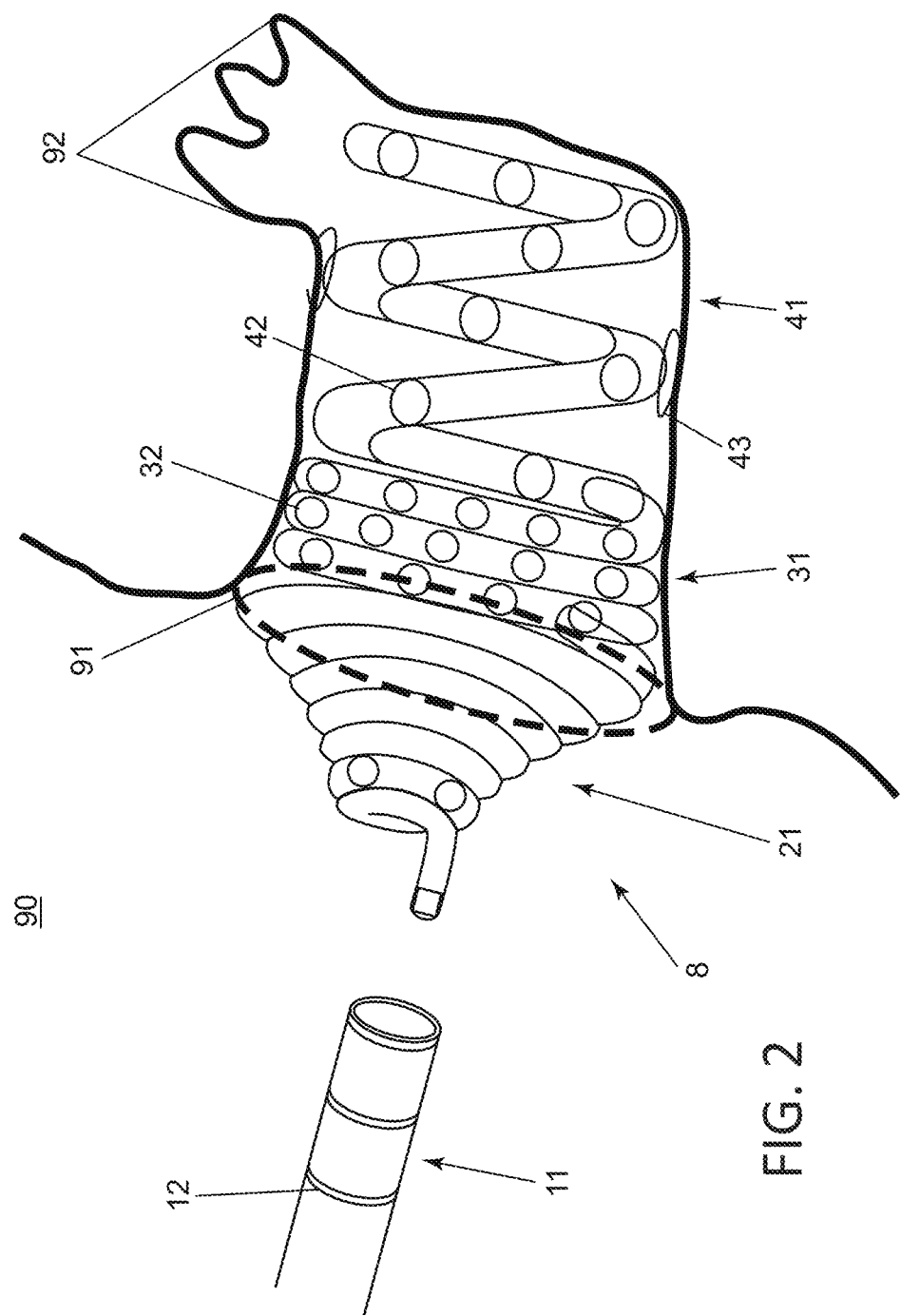
FIG. 2 is a cross-sectional view of a region of a heart showing the device of FIG. 1 being introduced into a left atrial appendage of the heart.

FIG. 2 is a cross-sectional view of a portion of a patient's heart, showing the device 8 of FIG. 1 located within a left atrial appendage 92 adjacent a left atrium 90 of the heart. As shown, a distal end of the deployment sheath 11 carrying deployment sheath electrodes 12 may be introduced into the patient's body, e.g., percutaneously into the patient's vasculature, and advanced into the LA 90 and into the LAA 92, e.g., by manipulating a proximal end of the sheath 11 (not shown), to introduce and deploy the components 21, 31, 41 of the device 8. For example, as shown, when the device 8 is fully deployed, the occluding portion 21 has been coiled like a rounded pyramid or cylindrical coil to cover the left atrial appendage ostium 91. The ablation/compression portion 31 is located at the ostium 91 distal to the occluding portion 21 in order to injure the tissue to facilitate electrical isolation of the LAA 92. The ablation/compression portion 31 includes one or more ablation/compression portion electrodes 32 to perform ablation on the tissue. In another embodiment, the ablation portion may include one or more electrodes or other elements 32 that enable laser therapy or electroporation to isolate tissue at the left atrial appendage ostium 91, or may use ultrasound to deliver ablation energy to the tissue.

The anchoring portion 41 is deployed deep within the LAA 92, i.e., distally beyond the ablation/compression portion 31, with anchoring portion tines 43 and anchoring portion electrodes 42 to help guide the device into the LAA 92.

Figure 3:
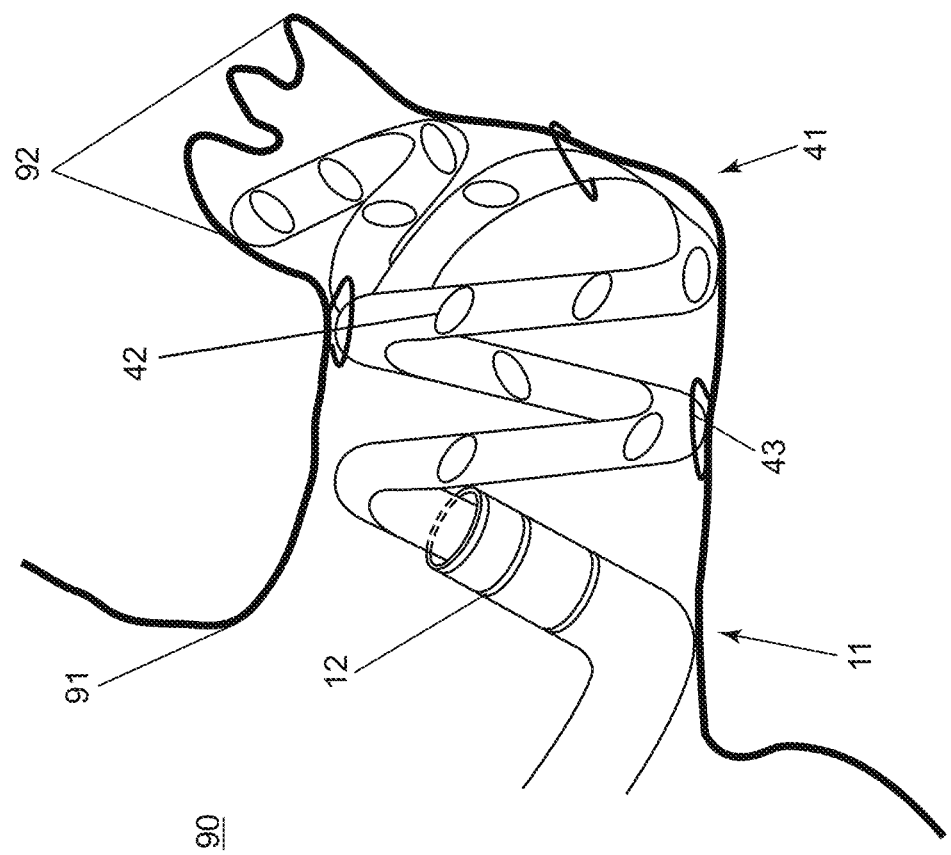
FIG. 3 is a schematic illustration of the device of FIGS. 1 and 2 being deployed.

FIG. 3 shows an exemplary method for sequentially deploying the components of the device 8 within the left atrial appendage 92. In this embodiment, the deployment sheath 11 with deployment sheath electrodes 12 may be used, first, to deploy the anchoring portion 41 of the device 8 into the deep aspects of the LAA 92. In the exemplary embodiment shown, the anchoring portion 41 may be a spiral catheter that may be enlarged to enable optimal contact and force against the cardiac tissue. The anchoring portion tines 43 are used to prevent embolization and anchoring portion electrodes 42 are used for positioning and deployment of the anchoring portion 41. In some embodiments, the anchoring portion electrodes 42 may be used to verify LAA 92 electrical isolation, e.g., by a controller (not shown) communicating with the electrodes 42. In another embodiment, the anchoring portion electrodes 42 may also deliver energy to ablate cardiac tissue, e.g., via a power source operated via the controller.

In this embodiment, a distal portion of the deployment sheath 11 may have a predetermined shape, e.g., biased to include a bend or angle, e.g., an acute angle not more than ninety degrees, proximal to the electrodes 12 to facilitate device deployment. In another embodiment, the bend may be able to rotate freely along the axis of the deployment sheath 11. In yet another embodiment, the angle may be controlled to a certain angle, e.g., using a steering element (not shown) extending from the distal portion to an actuator on the proximal end of the sheath, and/or the rotation may be controlled e.g., by rotating the proximal end of the deployment sheath 11 from outside the patient's body.

Figure 4:
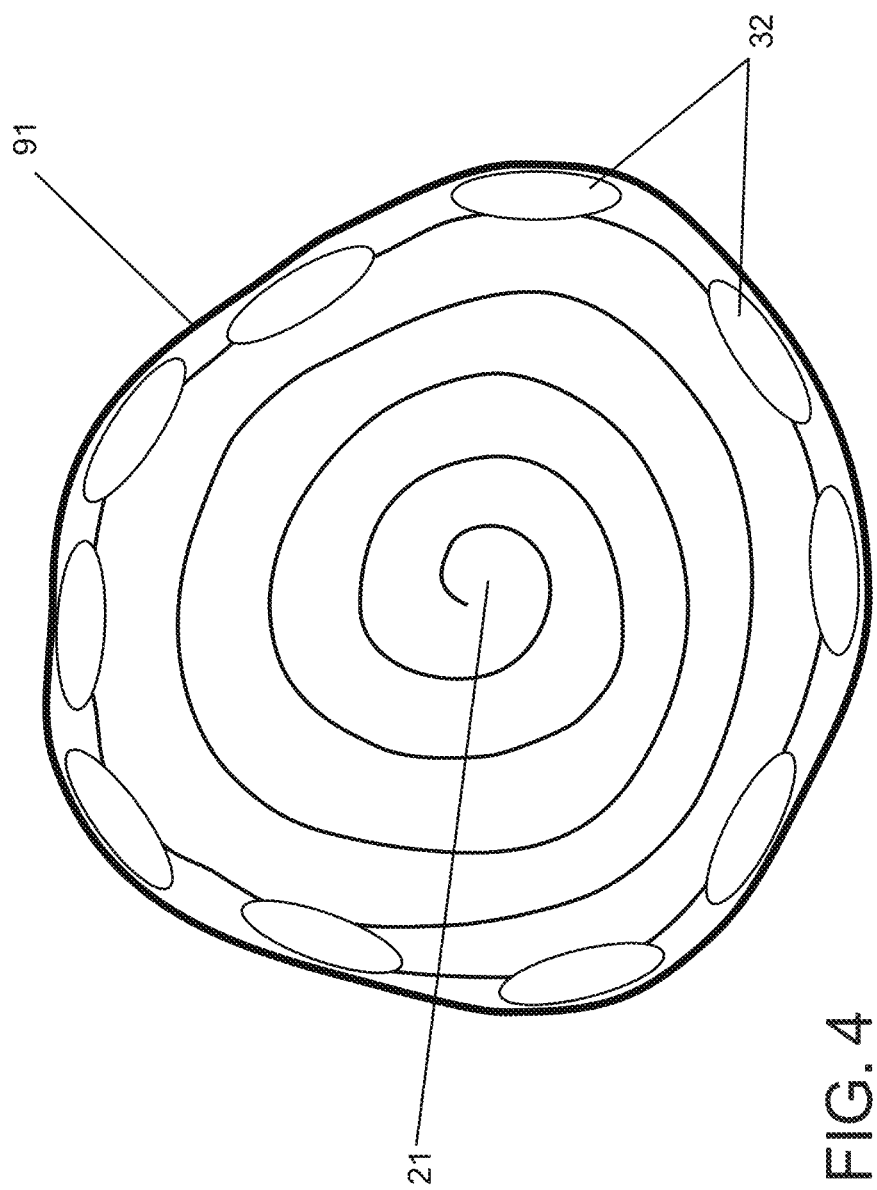
FIG. 4 is a schematic illustration of a view of the device of FIGS. 1-3 fully deployed within the left atrial appendage as seen from the left atrium.

FIG. 4 is a cross-sectional view showing the device 8 deployed within the LAA looking at the ostium of the LAA en face. The ablation/compression portion electrodes 32 are aligned along the LAA ostium 91. In one embodiment, the electrodes may be configured to deliver RF energy between the electrode and a grounding pad (e.g., in a uni-polar configuration). In addition or alternatively, RF energy may be delivered between two different electrodes (e.g., in a bi-polar configuration). By performing numerous ablations between one electrode and the ground; as well as each electrode to its closest neighbors, the LAA may be successfully electrically isolated. The closest neighboring electrode may be the electrode next along the device length, or against the closest electrode in the neighboring loop.

The ablation/compression portion 31 may be spring loaded, e.g., to a diameter or other cross-section larger than the LAA, such that it may be released to create radial force against the LAA ostium 91. In another embodiment, the ablation/compression portion 31 may have an inner cable or plunger (not shown) to enlarge the spiral/coils in order to control the size and resulting radial force. After the ablation/compression portion 31 is successfully positioned in the LAA 92, the occluding portion 21 may then be positioned to form a spiral pyramid to completely occlude the LAA 92 from the left atrium.

Figure 5:
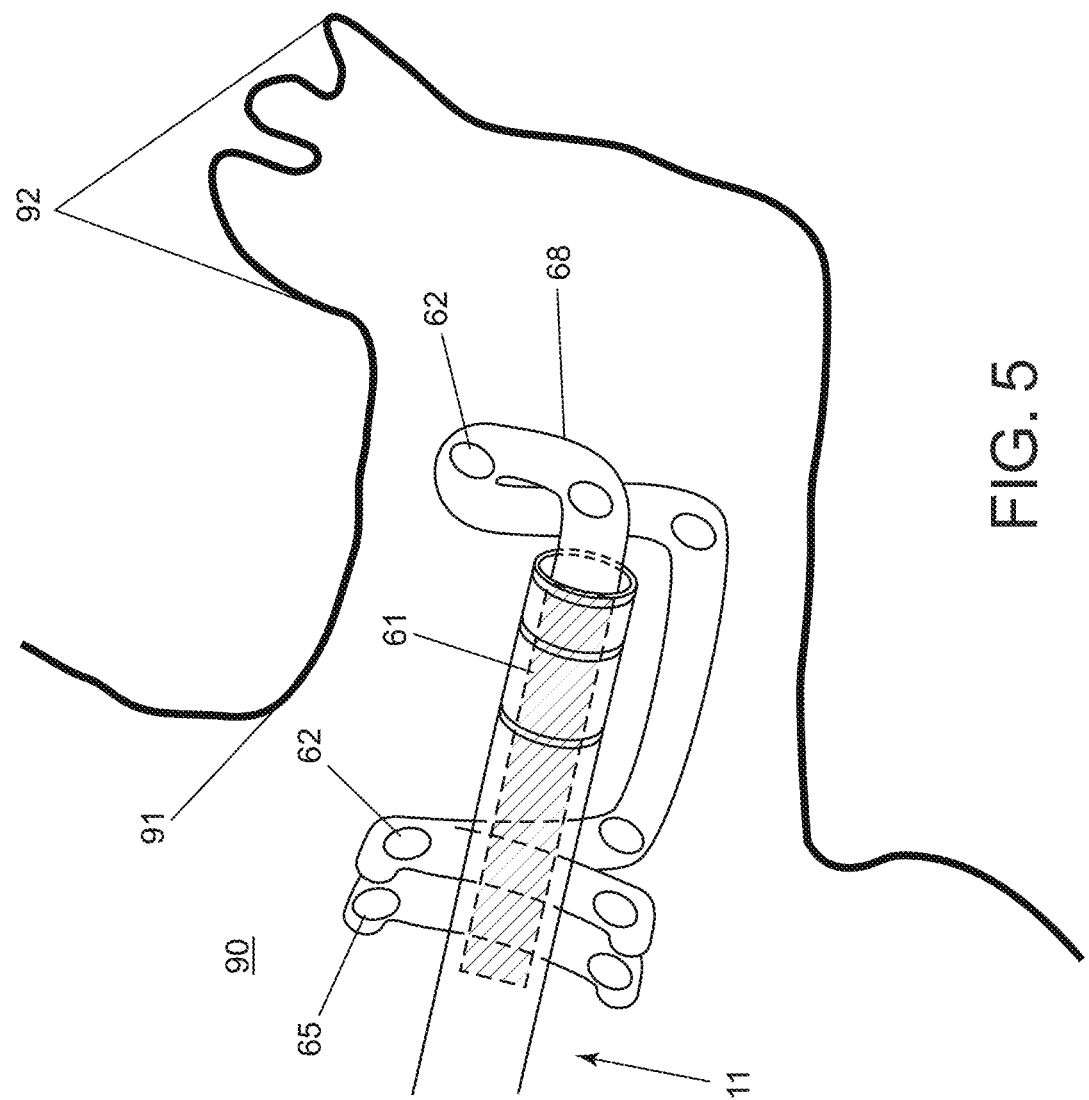
FIG. 5 is a cross-sectional view of a region of a heart showing another embodiment of a leadless pacemaker advancing into the left atrial appendage after conformational change within the left atrium.
Figure 6:
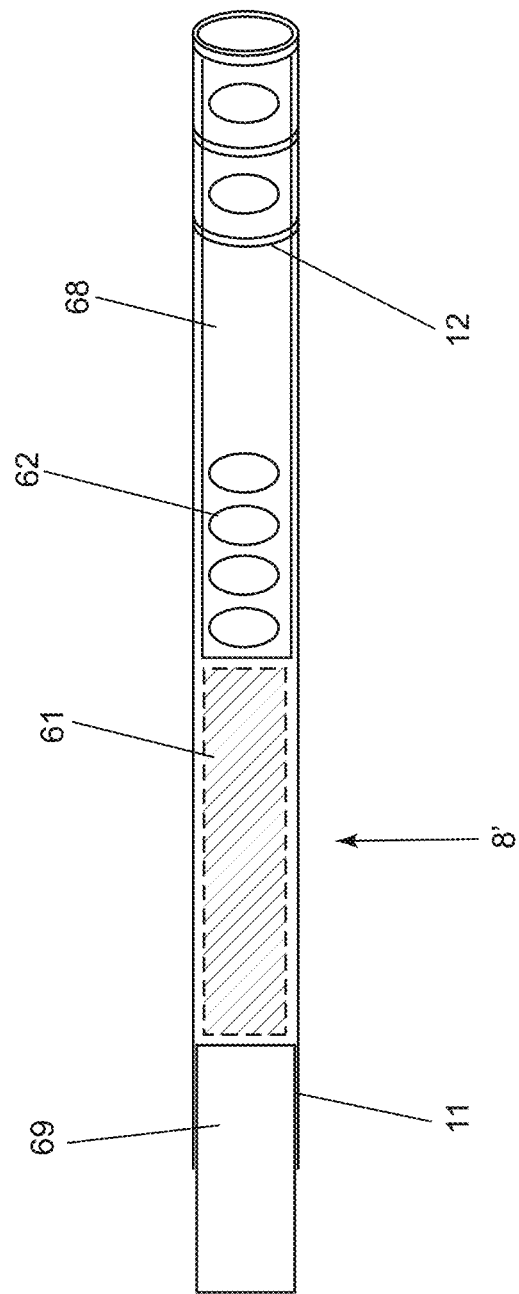
FIG. 6 is a schematic illustration of an exemplary embodiment of a device for electrical isolation of a left atrial appendage before deployment.

Turning to FIGS. 5-6, another embodiment of a device 8' is shown for electrical isolation of a left atrial appendage 92. In this embodiment, the device 8' includes an expanding portion 61, e.g., made of nitinol or other metal, such that the self-expanding portion 61 self-expands in blood, similar to a sponge. In one embodiment, the expanding portion 61 has an elongate member 68 extending from a distal end of the expanding portion 61. The elongate member 68 may have one or more guiding electrodes 62, e.g., a plurality of electrodes spaced apart along its length. In addition, one or more ablation electrodes 65, e.g., a plurality of spaced-apart electrodes, may also be provided on the elongate member 68. The elongate member 68 may be biased to coil around a distal portion of a deployment sheath 11 used to deliver and/or deploy the device 8'. The ablation electrodes 65 may also function as guiding electrodes 62 and are not mutually exclusive in any embodiment.

In this embodiment, the device 8' may be advanced into the deployment sheath 11, e.g., through a lumen of the deployment sheath 11 previously positioned within the left atrium 90. Once inside the left atrium 90, the device 8' may be advanced such that the elongate member 68 with guiding electrodes 62 extends out of the tip of the deployment sheath 11, e.g., as shown in FIG. 5. The elongate member 68 may automatically coil in front of the self-expanding portion 61 to help deployment into the LAA 92. In another embodiment, the elongate member 68 may automatically coil around the deployment sheath 11 once deployed. By surrounding the sheath 11 with electrodes 62, the deployment sheath 11 may be safely advanced into the LAA 92, e.g., using external imaging and/or mapping, similar to other embodiments herein. In addition, the guiding electrodes 62 may be seen on a mapping system to make sure the device 8' and deployment sheath 11 have the correct orientation when advanced into the LAA 92.

In one embodiment, the expanding portion 61 is self-expanding, e.g., formed from superelastic and/or temperature-activated material that is biased to assume the coil shape when deployed from the sheath 11 within the left atrium 90. In another embodiment, the expanding portion 61 may be expanded using to an external force, including inflating a balloon, delivering current through the material, or using a plunger/mechanical mechanism (not shown).

Once the deployment sheath 11 is advanced into the LAA 92, the guiding electrodes 62 may enlarge, uncoil, or change shape to facilitate contact with the LAA 92 tissue. RF energy may then be delivered through the guiding electrodes 62 to electrically isolate the LAA 92. Next, the deployment sheath 11 may be withdrawn, exposing the expanding member 61 within the LAA 92, e.g., within the ostium 91. The expanding member 61 may then expand and completely occlude the LAA 92 from the rest of the left atrium 90. The expanding member 61 then locks the device 8' within the LAA 92.

Optionally, the expanding member 61 may include material to facilitate endothelialization. In another embodiment, a cover may be provided proximal to the expanding member 61 to completely occlude the LAA 92 from the LA 90. The expanding member 61 may be designed to deliver radial force to isolate the LAA 92 through compression, e.g., similar to other embodiments herein. In another embodiment, a covering disc 69 (not shown, see FIG. 6) is positioned proximal to the expanding member 61 to deliver radial force to isolate the LAA 92. The covering disc may also occlude the LAA 92 from the rest of the LA 90.

A useful aspect of the device 8' shown in FIG. 5 is that the device 8' is deployed within the LA 90 such the device 8' makes a conformational change within the LA 90 before it is advanced into the LAA 92. Current LAA devices are generally designed to have the device deployed directly into the LAA 92. A unique aspect of the device 8' is that it is deployed into the LA 90 and then changes shape before being advanced into the LAA 92. This confirmation change may be easily performed within the open space of the LA 90 without being confined to the LAA 92 structure, which is known to be quite friable. By enabling the device 8' to be deployed and change shape within the LA 90, new opportunities are available to positioning the device 8'. Similar to a ship-in-a-bottle, the device 8' may be prepared in the LA 90 and then advanced and deployed into the LAA 92.

FIG. 6 is a cross-sectional view of a distal end of the deployment sheath 11 including the device 8' positioned within a lumen of the deployment sheath 11. In this embodiment, the covering disc 69, the enlarging member 61, the elongate member 68 with guiding electrodes 62 are all positioned sequentially within the lumen of the deployment sheath 11. As the device 8' is advanced, the elongate member 68 initially is deployed and coils. The elongate member 68 includes electrodes 62 to guide the deployment sheath 11 into the LAA ostium 91. The elongate member 68 may then bend into a certain pre-specified structure. Similar to a ship-in-a-bottle, the elongate member 68 may assume a complex shape to facilitate the deployment sheath 11 into the LAA 92, position the device 8' optimally, expand to deliver radial force against the ostium of the LAA 91, and/or deliver RF energy. The expanding member 61 may then further lock the device 8' into place.

Figure 7:
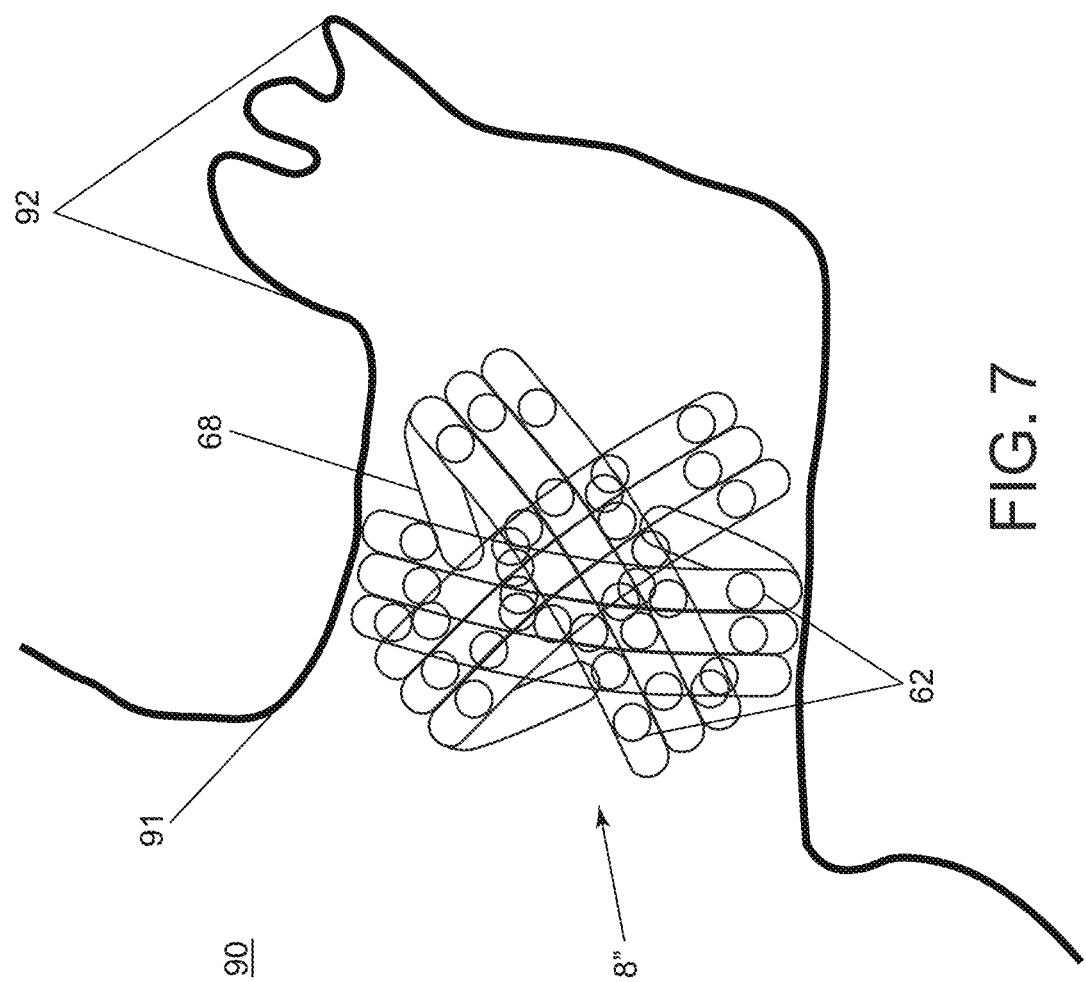
FIG. 7 is a cross-sectional view of a region of a heart showing another embodiment of a device for electrical isolation of a left atrial appendage of the heart after deployment.

Turning to FIG. 7, another embodiment of a device 8" is shown for electrical isolation of a left atrial appendage 92 generally similar to other embodiments herein. In this embodiment, the device 8" includes an elongate member 68 including one or more electrodes 62, e.g., a plurality of spaced-apart electrodes similar to other embodiments herein. After leaving the deployment sheath (not shown), the elongate member 68 coils into a predetermined shape, e.g., a spherical shape, within the LAA 92. By having the elongate member 68 lined by electrodes 62 into a spherical structure, any orientation of the device 8" may be used isolate the LAA 92 electrically.

Figure 8:
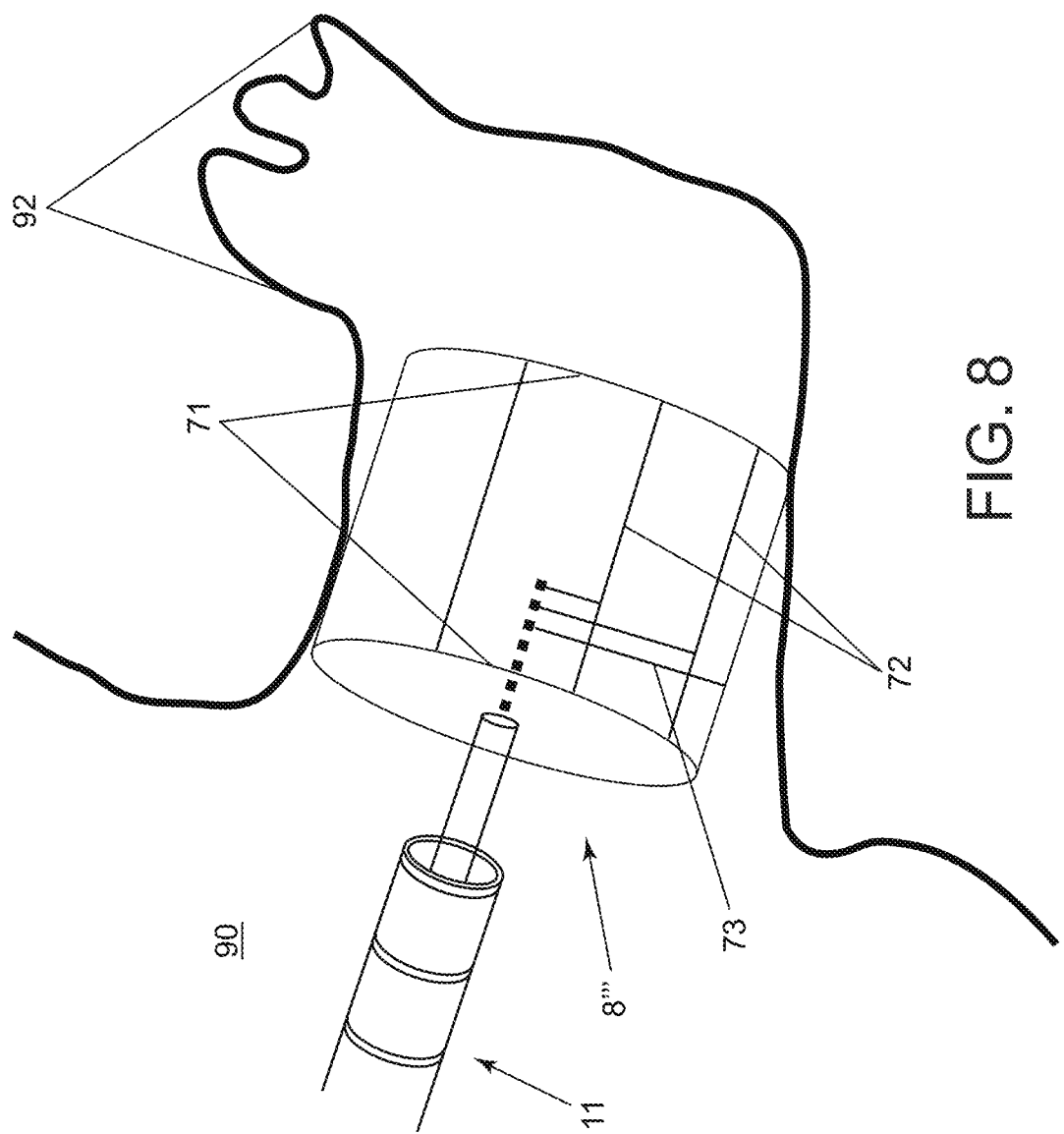
FIG. 8 is a cross-sectional view of a region of a heart showing yet another embodiment of a device being deployed within a left atrial appendage of the heart.

Turning to FIG. 8, another embodiment of a device 8''' is shown for electrical isolation of a left atrial appendage 92. In this embodiment, the device 8''' includes an expandable member 71 carrying one or more electrodes 72, e.g., a plurality of spaced apart electrodes. These electrodes 72 may be used to guide deployment as well ablate cardiac tissue to isolate the LAA 92, e.g., similar to other embodiments herein. The ablation may be performed utilizing ultrashort high voltage ablation, e.g., to induce electroporation to induce LAA 92 electrical isolation. The ablation electrodes 72 may be connected to the deployment sheath 11 through one or more connectors 73, which transmit electrical signals from an external controller (not shown) to the electrodes 72.

Figure 9:
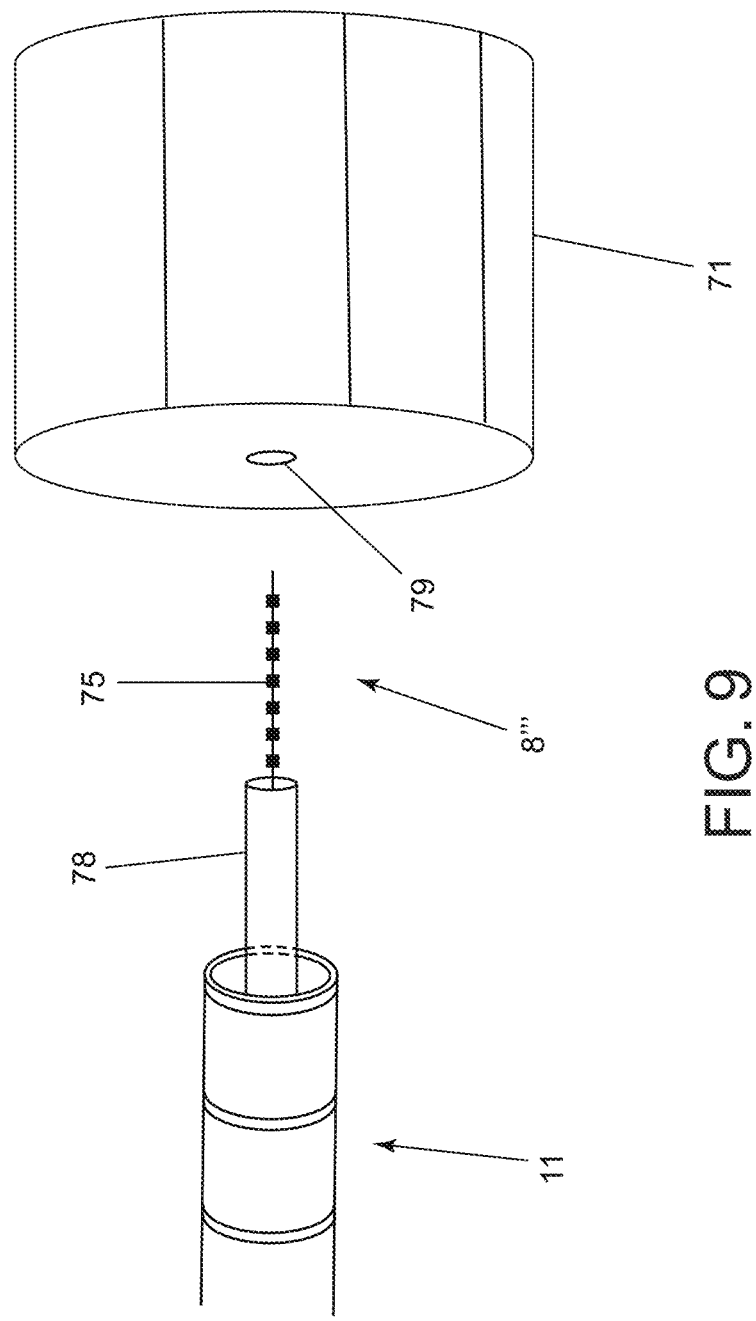
FIG. 9 is a schematic illustration of an exemplary embodiment of an electrical connection for a device for electrical isolation of a left atrial appendage, such as that shown in FIG. 8.

FIG. 9 is a schematic illustration of an exemplary embodiment of an electrical connection to the device 8''' shown in FIG. 8. The closure device 71 is transported through a lumen of the deployment sheath 11, e.g., previously introduced into the left atrium, similar to other embodiments herein. The closure device 71 maybe deployed using a plunger 78, e.g., movable relative to the sheath 11, that includes one or more connectors 75 to transmit electricity from the external controller.

The plunger 78 and closure device 71 may include one or more cooperating and/or detachable connectors for releasing the closure device 71 from the plunger 78 after deployment. For example, in an exemplary embodiment, the plunger 78 and closure device 71 may include mating threads such that the plunger 78 may be rotated to disconnect the closure device 71. After the plunger 78 and connectors 75 are disconnected and withdrawn, a cap 79 covers the connection site between the connectors 75 and the closure device 71.

Turning to FIGS. 10 and 13-16, another embodiment of a deployable device 8G is shown including an elongate spiraling member 110 carrying one or more batteries 117, a controller or processor 120, and a cover 130, e.g., formed from Nitinol or other elastic material. As shown, a delivery sheath 11 may be used to deliver the device 8G, e.g., to sequentially deploy the components to isolate the LAA 92. Optionally, the spiraling member 110 may include one or more tines 113, e.g., to help stabilizing the device 8G within the LAA 92. In the embodiment shown, the spiraling member 110 may carry a plurality of battery subunits 117 connected to one another by connectors or electrodes 112, e.g., in series. The connectors 112 may be flexible to allow the spiraling member 110 to spiral or fold upon deployment. In other embodiments, the connectors 112 may include electrodes, which may be configured to be visualized on a mapping system. In addition, the connectors 112 may be coupled to the processor 120, e.g., to deliver ablation energy to electrically isolate the left atrial appendage, similar to other embodiments herein. Optionally, the connectors 112 may also measure local electrical activity. For example, connectors 112 in the proximal portion of the LAA 92 may deliver ablation energy, while connectors 112 in the distal portion of the LAA 92 may be used to identify that the LAA 92 has been successfully electrically isolated. Optionally, some of the distal connectors 112 may also deliver electrical energy to facilitate adherence or attachment to tissue. The energy may be delivered while the connectors 112 are in contact with the LAA 92, thereby making the tissue 'stick' to the connectors 112. In another embodiment, the created heat may be used to cause a confirmation change in the tines 113 to have better contract or even screw into the LAA 92.

The spiraling member 110 may also house the battery units 117 for the device 8G. In general, the battery units 117 may be made similar to components that power other implantable devices, including but not limited to lithium-metal, lithium-ion, silver oxide, lithium iodide, and lithium/manganese dioxide. In some embodiments, the batteries are firm; in other embodiments the batteries are flexible to facilitate deployment. In other embodiments, the spiraling member 110 is able to create electrical energy from heart movement. In other embodiments, the device 8G may be powered by ultrasound or electromagnetic energy.

In some embodiments, the spiraling member 110 includes a series of repeating battery subunits 117 that are flexible. However, not all batteries are flexible. Therefore, in order for the battery subunits 117 to change shape to fit and/or attach within the LAA 92, the battery subunits 117 may not be flexible but the connectors 112 are flexible. In some embodiments of the device 8G, the battery portion of the elongate member 110 includes at least two or more similar repeating subunits 117. These battery subunits 117 are connected by one or more connectors 112. The connector 112 enables a hinge point that allows the battery subunits 117 to change orientation for deployment within the LAA 92.

The device 8G may be deployed from the distal end of the delivery sheath 11 using a plunger 140, e.g., movable within a lumen of the sheath 11. In some embodiments, the plunger 140 may include inner connecting wires (not shown), e.g., coupled to the connectors 112 until the device 8G is released. In the exemplary embodiment shown, the plunger 140 on the distal end includes a screw 122 that may be turned to release the plunger 140 from the rest of the device 8G, although it will be appreciated that other releasable connectors may be used, e.g., similar to other embodiments herein.

In some embodiments, the device 8G includes a cover portion 130 designed to prevent thrombus from leaving the LAA 92. This cover portion 130 may be configured to enclose most or all of the device 8G within the LAA 92, e.g., expand across the ostium 91 of the LAA 92, similar to other embodiments herein. Any blood clots that form within the LAA 92 are then trapped within the LAA 92 and cannot embolize. The cover portion 130 may include one or more sensors that help measure left atrial pressure or physical movement.

Optionally, the cover portion 130 may also include one or more pacing electrodes 132. The pacing electrode(s) 132 enable the device 8G to sense and pace the heart even if the LAA 92 is electrically isolated. For example, the cover portion 130 may be designed to extend beyond the ostium 91 of the LAA 92 to contact atrial tissue within the main chamber of the left atrium 90. Therefore, when the cover portion 130 covers the LAA 92, the pacing electrodes 132 may contact atrial tissue outside the LAA 92. These pacing electrode(s) 132 may be a few millimeters away from the ostium 91 of the LAA 92 or extend several millimeters away from the ostium 91 of the LAA 92. This enables the proceduralist to freely electrically isolate the LAA 92 without concern that the device 8G will not be able to sense and pace the heart. In some embodiments, the cover 130 is able to freely rotate relative to the processor 120. This enables the cover 130 to completely close off the LAA 92. In addition, this enables the cover 130 to be pulled back and rotated to reposition the pacing electrodes (132). This may be done if the pacing electrodes (132) do not have adequate sensing and capture parameters to adequately sense and pace the heart, respectively. In some embodiments, the pacing electrodes 132 extend outward from the cover portion 130 to facilitate good tissue contact.

Figure 11:
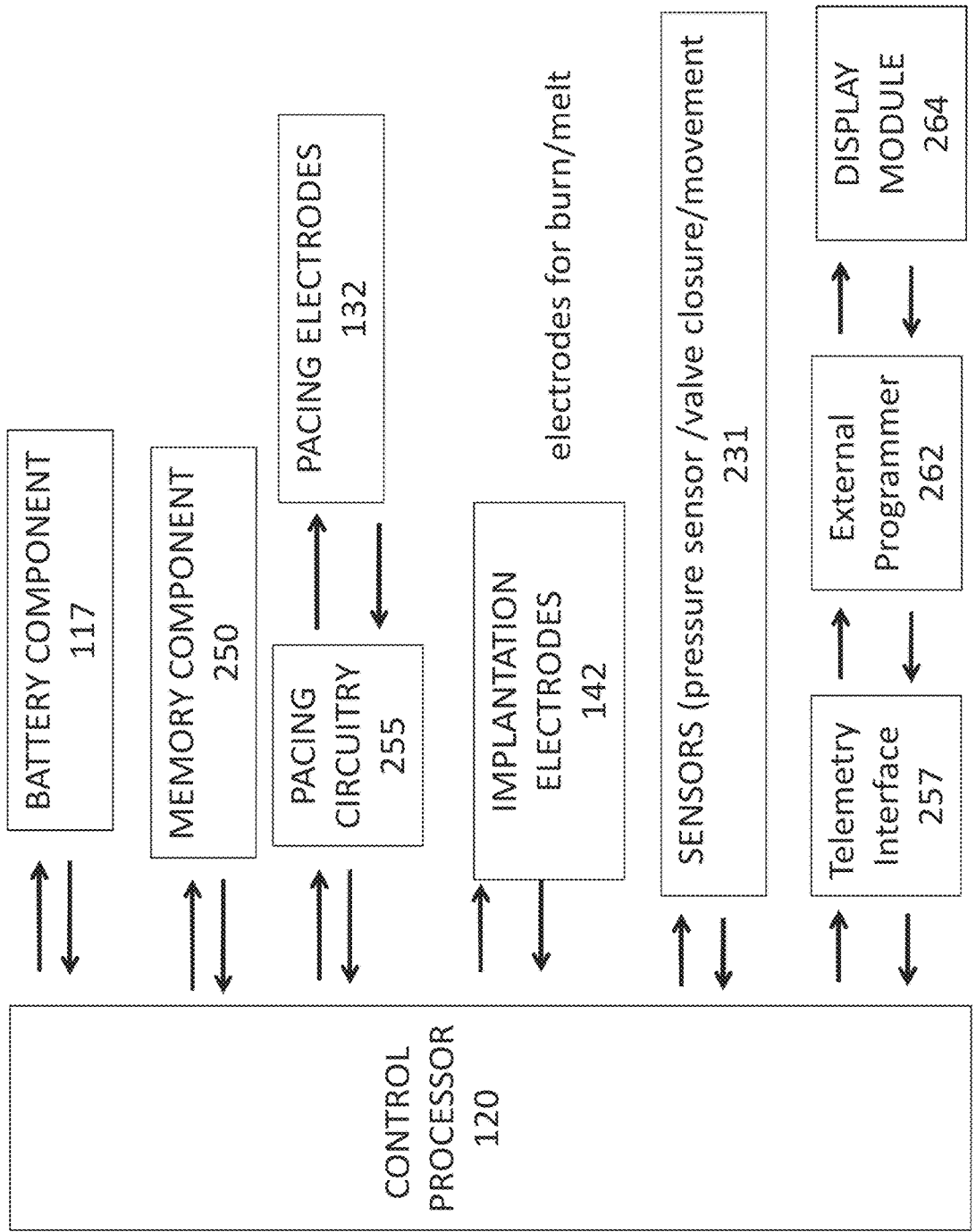
FIG. 11 is a simplified functional block diagram of an exemplary embodiment of a leadless pacemaker device.

FIG. 11 shows a simplified functional block diagram of one embodiment of the device 8G. The components include the control processor 120, battery component 117, memory component 250, pacing electrodes 132, implantation electrodes 142, various sensors 231, and a telemetry interface 257. The control processor 120 receives input information from various components in order to determine the function of the different components to treat the patient. The pacing electrodes 132 are used to sense and pace the heart. The pacing electrodes 132 are coupled to pacing circuitry 255 that is coupled to the control processor 120.

Optionally, the device 8G may include one or more implantation electrodes 142, which may visualized by a mapping system in order to help deploy the device 8G within the LAA 92, similar to other embodiments herein. In addition, optionally, the implantation electrodes 142 may be used to deliver electrical or electroporation energy in order to electrically isolate the LAA 92. In other embodiments, the implantation electrodes 142 may deliver energy to help attach the electrodes 142 to LAA 92 tissue to prevent device 8G embolization.

The processor 120 may also be connected to one or more sensors 231. In one embodiment, the sensors include a three-axis accelerometer. Signals from the three-axis accelerometer may be used by the processor 120 to detect patient activity in the presence of cardiac motion. Alternative sensors 231 may include vibration or movement sensing abilities, which may sense sound or vibrations, e.g., to correlate with valve closure. By determining valve closure, the device 8G may determine what the ventricle of the heart is doing. In another embodiment, one or more temperature and/or movement/accelerometer sensors may be provided that may be coupled to the processor 120 to determine if the patient is exerting or moving in order to determine the pacing rate of the device 8G.

In another embodiment, the device 8G may include one or more sensors 231 that correlate with the blood pressure within the left atrium 90. These sensor(s) 231 may help identify a heart failure admission similar to the CardioMEMs device. These sensor(s) 231 may also be used to optimize medical therapy. In another embodiment, various measurements between electrodes are used to guide device 8G therapy. Both near-field and far-field electrical activity may be used to determine atrial and ventricular activity as well as diagnose conduction abnormalities.

The pacing circuitry 55 connects to pacing electrodes 132 to the control processor 120. These connections allow for multiple capacities to sense electrical activity (such as myocardial depolarizations), deliver pacing stimulations, and/or deliver defibrillation or cardioversion shocks. The control processor 120 may be connected to a telemetry interface 257. The telemetry interface 257 may wirelessly send and/or receive data from an external programmer 262, which may be coupled to a display module 264 in order to facilitate communication between the control processor 120 and other aspects of the system external to the patient.

Figure 12:
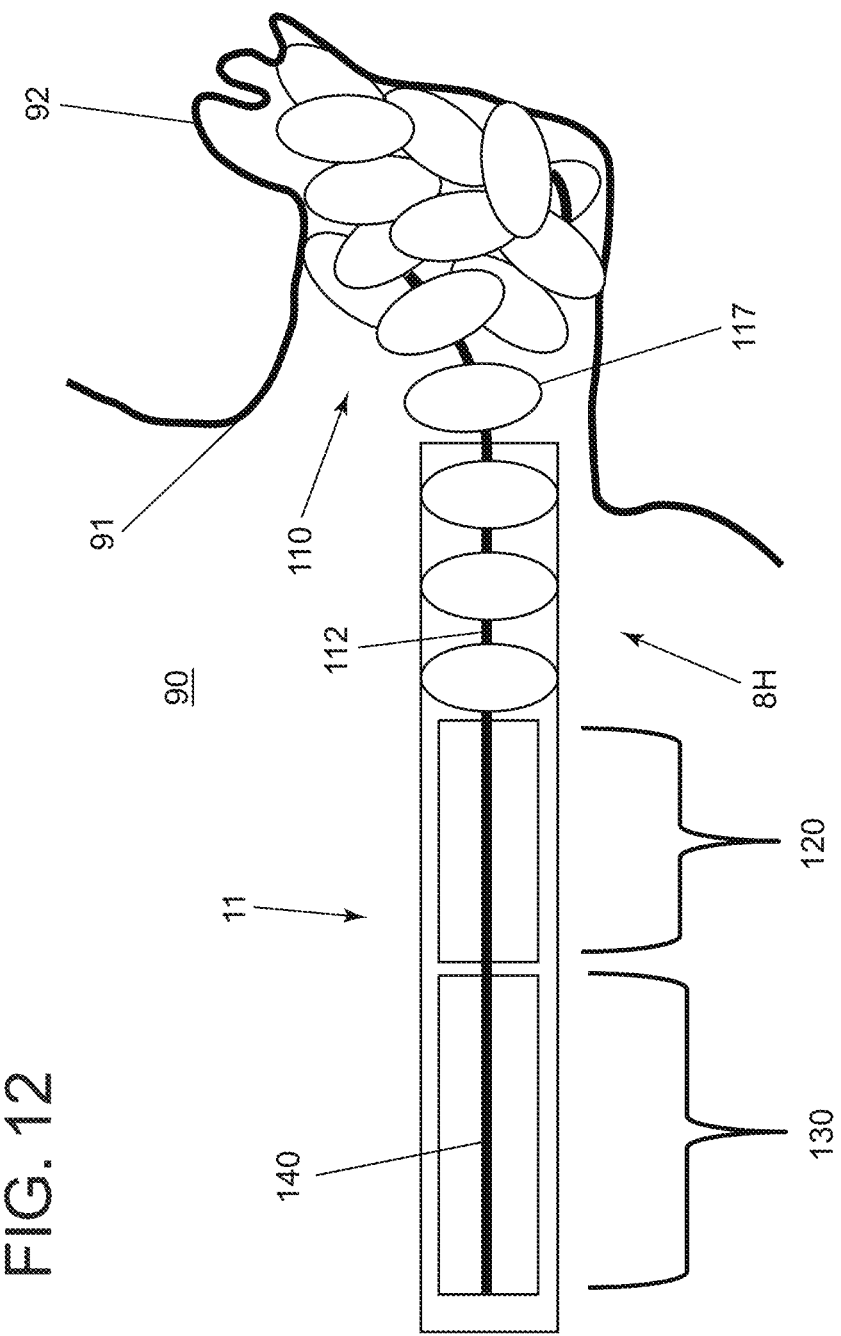
FIG. 12 is a schematic illustration of still another embodiment of a leadless pacemaker designed for implantation within the left atrial appendage.

Turning to FIG. 12, another exemplary embodiment of a leadless pacemaker device 8H is shown that generally includes an elongate member 110 carrying battery subunits 117, a processor 120, and a cover 130, configured to be deployed sequentially from a delivery sheath 11 for implantation within the left atrial appendage (LAA) 92, generally similar to other embodiments herein. In this embodiment, the battery subunits 117 are connected by flexible connectors 112 that allow the batteries 117 to fold on themselves. In this manner, the elongate member 110 carrying the battery subunits 117 may be advanced out of the delivery sheath 11 and packed into the LAA 92. After the battery subunits 117 have been advanced into the LAA 92, the processor 120 may be advanced into the LAA 92. Finally, the cover portion 130 may be placed over the ostium of the LAA 92. Optionally, in some embodiments, the device 8H may include a separate anchor system (not shown) that anchors the device 8H into the LAA 92. In another embodiment, the connectors 112 are set to lock in place. By locking in place, the entire structure is locked into position within the LAA 92. In some embodiments, the elongate member 110 may include a plurality of tines (not shown) that help attach the device 8H within the LAA 92.

Figure 10:
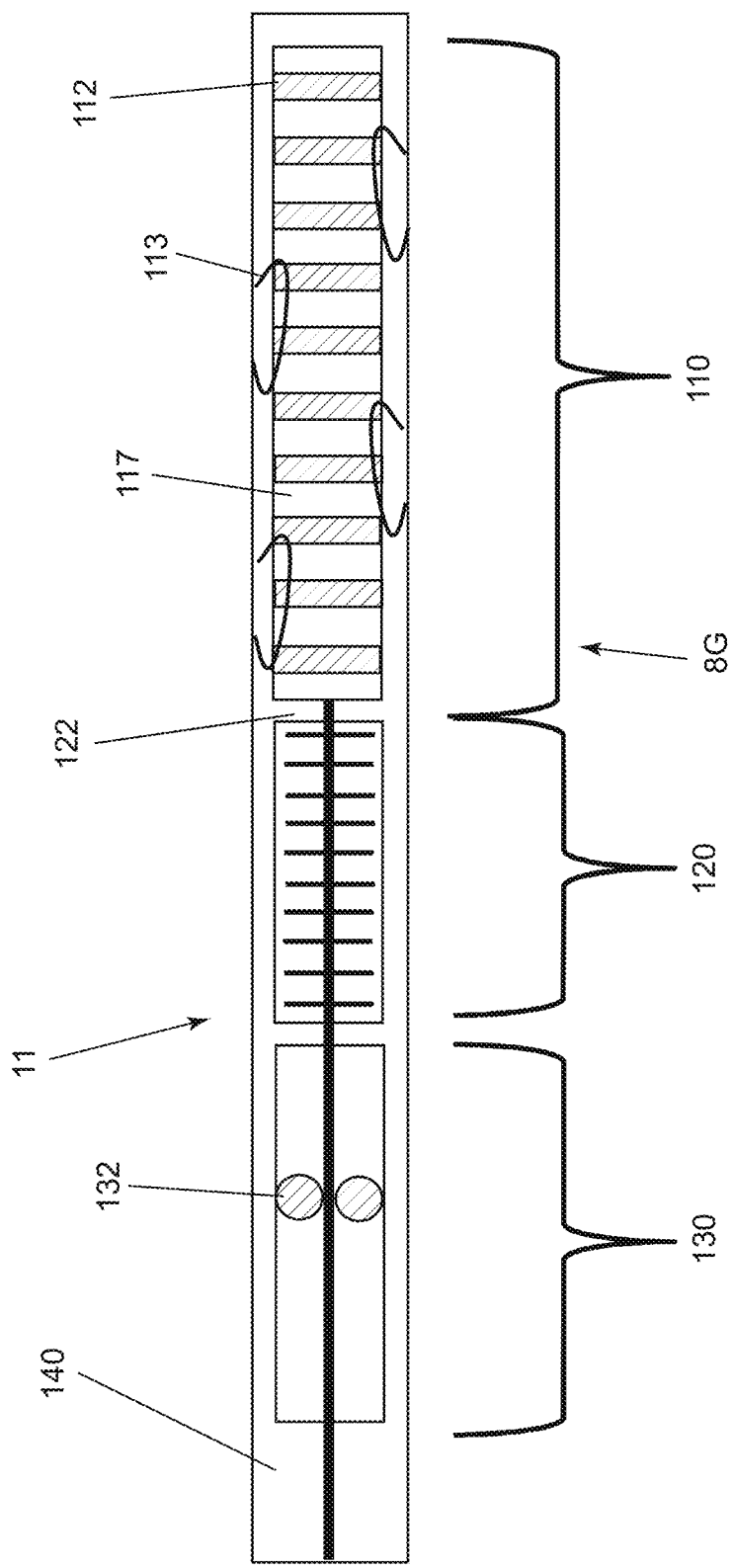
FIG. 10 is a schematic illustration of another embodiment of a leadless pacemaker device designed for implantation within or near a left atrial appendage.
Figure 16A:
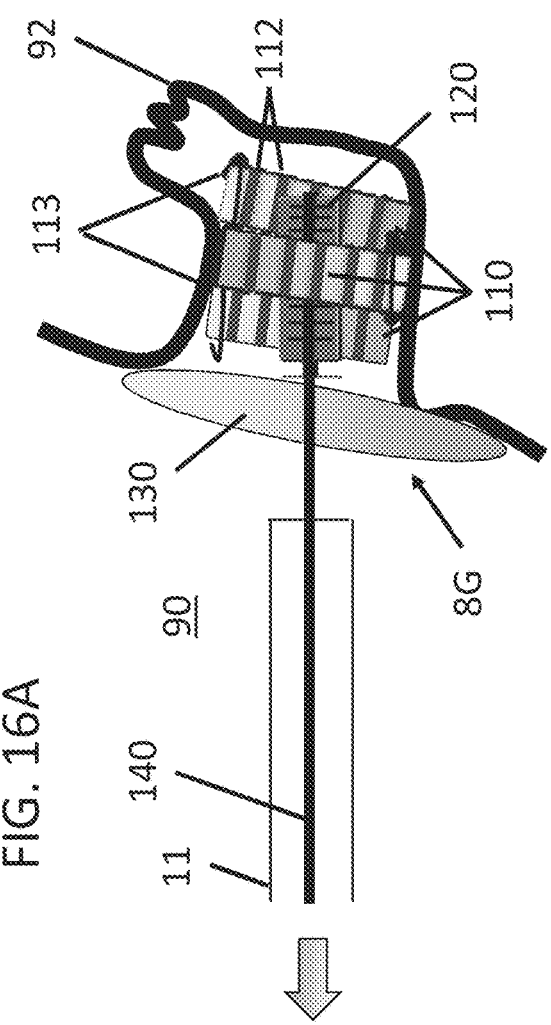
Figure 16B:
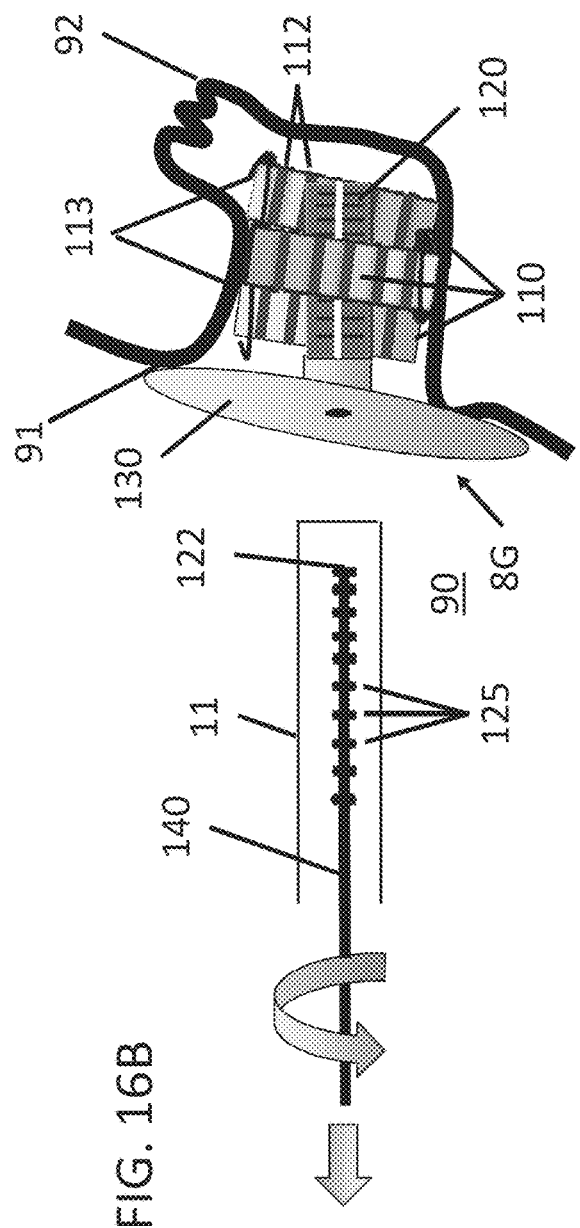

Turning to FIGS. 13A and 16B, an exemplary method is shown for deploying the device 8G shown in FIG. 10. Initially, as shown in FIG. 13A, the distal end of the delivery sheath 11 may be advanced to the ostium 91 of the left atrial appendage 92. The plunger 140 is then moved relative to the delivery sheath 11, e.g., advanced while the delivery sheath 11 is held stationary. Moving on to FIG. 13B, as the spiraling member 110 is deployed from the delivery sheath 11, the spiraling member 110 coils around the ostium 91 of the left atrial appendage 92. In some embodiments, the delivery sheath 11 has a curved distal end. The distal end of the delivery sheath 11 may help position the spiraling member 110 against the tissue of the left atrial appendage 92.

As shown, the spiraling member electrodes 112 may be evenly spaced along the spiraling member 110. In other embodiments, the spiraling member electrodes 112 are not evenly spaced. For example, the spiraling member electrodes 112 may be more closely spaced adjacent the distal end in order to have more electrodes located near the proximal portion of the left atrial appendage 92, while there may be just a few spiraling member electrodes 112 more proximally which are then positioned deeper into the left atrial appendage 92. This is because in some embodiments, as the plunger 140 is advanced, this action several loops of the spiraling member 110 to coil deeper and deeper into the left atrial appendage 92.

In some embodiments, a mechanism as used to dilate the spiraling member 110. In one embodiment, the spiraling member 110 is placed entirely within the left atrial appendage 92, and then the coils are released to create a radial force outwardly. This radial force holds the spiraling member 110 firmly against left atrial appendage 112 tissue. This mechanism includes a spring mechanism that can be released as well as an inner cable (not shown) that can be pulled or pushed to dilate/enlarge the coils of the spiraling member 110.

Moving to FIG. 14A, the plunger 140 continues to be advanced while the delivery sheath 11 remains stationary. The spiraling member 110 continues to coil distally into the left atrial appendage 92. Moving onto FIG. 14B, the processor component 120 is advanced into the left atrial appendage 92. The processor component 120 may fit within an open central region of the spiraling member 110 after it's deployed. The connector component 110 may have stabilizing tines (not shown) to position the processor component 120 within the center of the spiraling member 110.

Figure 15A:
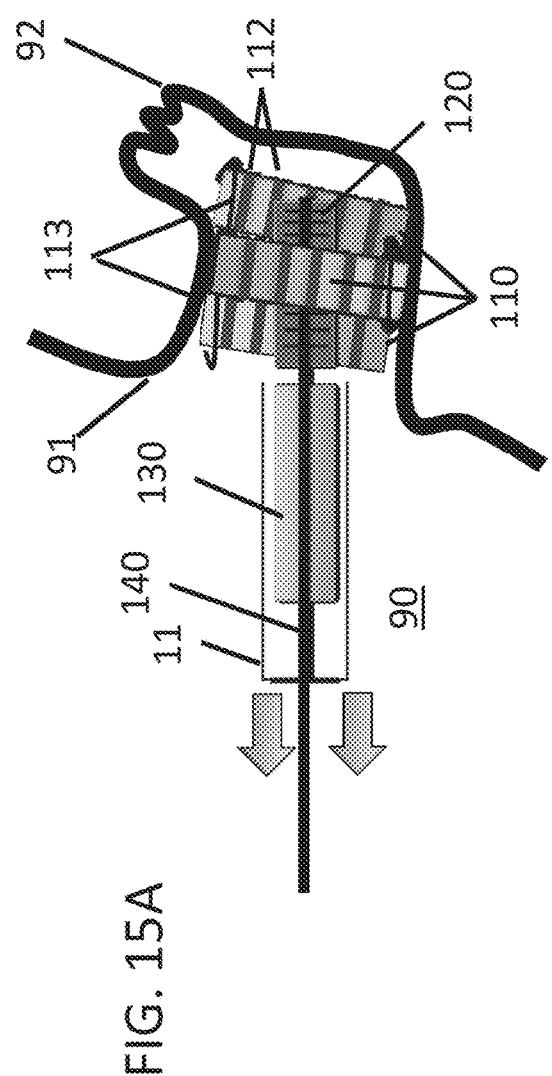

Moving on to FIG. 15A, the spiraling member 110 has several loops wrapping around the inside of the left atrial appendage 92. In addition, as shown, the processor component 120 is located within the spiraling member 110. In some embodiments, one or more indicators may be provided on the proximal end of the delivery sheath 11 located outside of the body (not shown), e.g., to indicate that the spiraling member 110 and processor component 120 should not be located entirely within the left atrial appendage 92. The deliver sheath 11 may then be withdrawn while the plunger 140 is fixed.

Figure 15B:
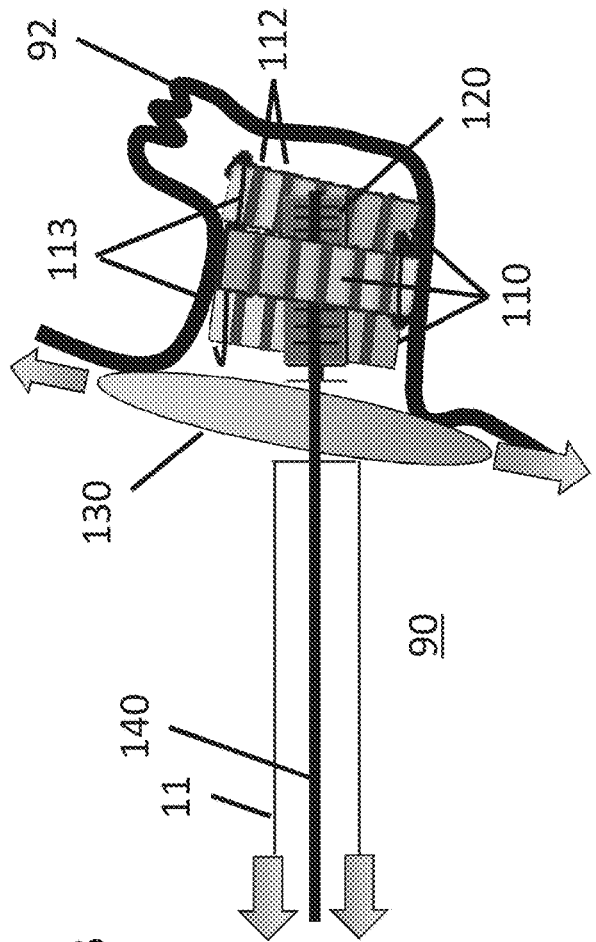

Moving to FIG. 15B, by withdrawing the deliver sheath 11 over the plunger 140, the Nitinol cover 130 is released. The Nitinol cover 130 is designed to self-expand. This causes the Nitinol cover 130 to cover the ostium 91 of the left atrial appendage 92. This Nitinol cover 130 may substantially occlude or otherwise isolate the left atrial appendage 92 from the rest of the left atrium (not shown).

Moving to FIG. 16A, the device 8G is now completely located within the left atrial appendage 92. The delivery sheath 11 may be withdrawn to provide space between the delivery sheath 11 and the device 8G. The plunger 140 may now be withdrawn to confirm the device 8G is firmly positioned within the left atrial appendage 92. This is a 'tug test' to verify the device is unlikely to dislodge and embolize.

Energy may then be delivered to the optimally positioned spiral member electrodes 112. This energy may ablate the proximal portion of the left atrial appendage 92 tissue to electrically isolate the left atrial appendage 92. More distal spiral member electrodes 112 may be used to monitor electrical activity from the left atrial appendage 92 to verify the left atrial appendage 92 has been electrically isolated.

Moving to FIG. 16B, the plunger 140 may then be rotated or otherwise manipulated to release the device 8G. For example, as shown, rotation spins the screw 122 to release the plunger 140 from the device 8G. The plunger 140 may then be withdrawn. The distal end of the plunger 140 includes connecting electrodes 125. These connecting electrodes 125 connect the inner wires within the plunger 140 to electrodes within the connector component 120. Once the plunger 140 leaves the Nitinol cover 130, the Nitinol cover 130 may have a self-closing valve (not shown) to completely close off the device 8G.

Turning to FIGS. 17A-19B, another embodiment of a device 8J is shown for electrical isolation of a left atrial appendage 92 generally similar to the device 8H shown in FIG. 12 with several differences. In this embodiment, instead of a connector component 122 described in FIG. 12, the device 8J includes a processor 170 electrically connected to the spiraling member electrodes 112, e.g., located between a spiraling member 100 carrying the electrodes 112 and a compression portion 180. In addition, the spiraling member 110 may be deployed from the distal end of the delivery sheath 11 whereupon the spiraling member 110 may automatically coil towards a preset shape. Once coiled inside of the left atrium 90, the sheath 11 may then be safely advanced towards the left atrium appendage 92.

Moving on to FIG. 17B, the device 8J may then be advanced deep into the left atrial appendage 92. The depth of the device 8J may be determined and verified using a mapping system (not shown), e.g., connected to the spiraling member electrodes 112 such that the mapping system receives signals from the electrodes 112 that may be analyzed to confirm the position of the spiraling member 110. The electrodes 112 may be coupled to the mapping system via wires that extend through the delivery sheath 11; alternatively, the signals may be sent wirelessly, e.g., via a wireless communications interface (not shown) communicating with the processor 170. A battery (not shown) for the processor 170 may be stored in the processor portion, e.g., mounted on a substrate (also not shown) that carries the processor 170. In another embodiment, the spiraling member 110 has energy stored within this segment. The spiraling member 110 may therefore also function as a battery. Once the spiraling member 110 and sheath 11 are optimally placed within the left atrial appendage 92, the spiraling member 110 may be enlarged to stabilize within the left atrial appendage 92.

Figure 18A:
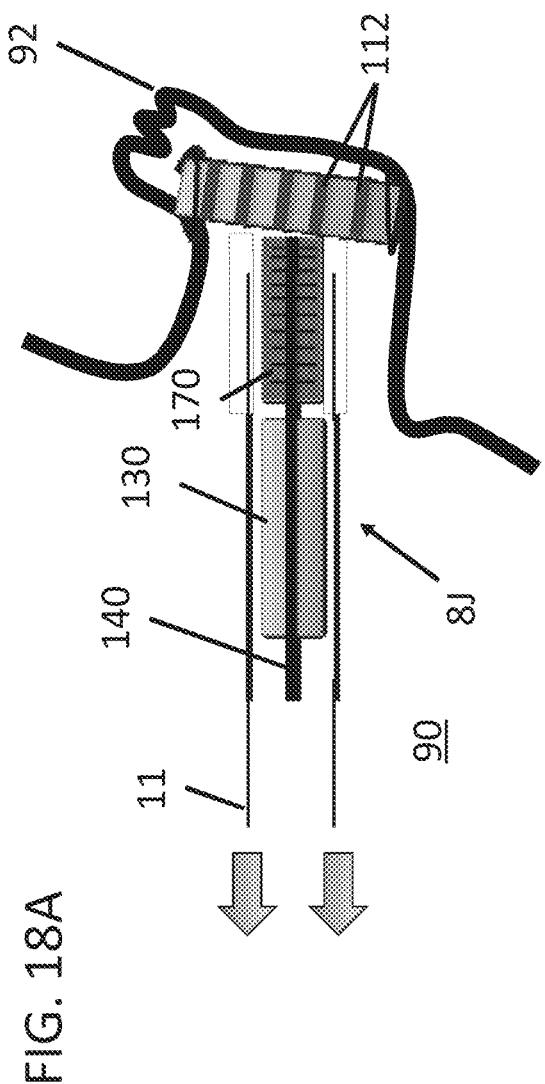
Figure 18B:
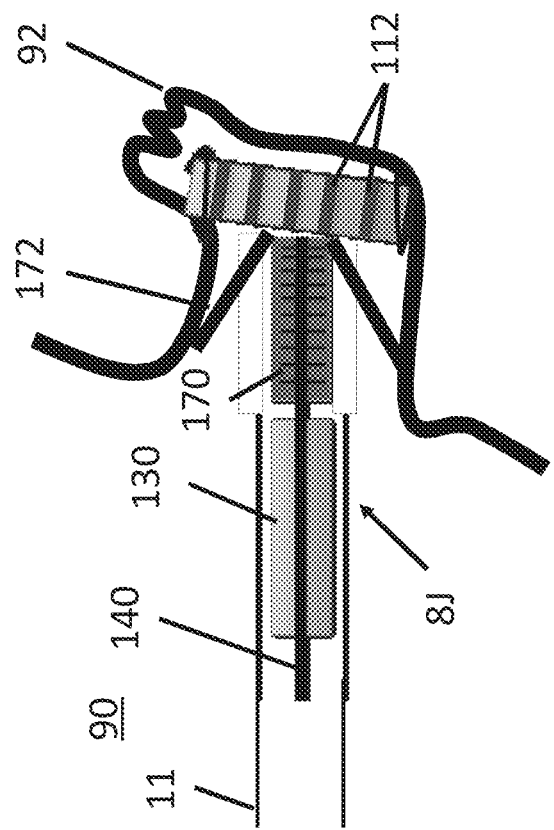

Moving on to FIG. 18A, once the spiraling member 110 is properly positioned, the delivery sheath 11 may be withdrawn, thereby releasing the processor 170 within the left atrial appendage 92. In some embodiments, the processor 170 itself may coil within the left atrial appendage 92 or the processor 170 may maintain its original linear orientation. Moving to FIG. 18B, as the delivery sheath 11 is further withdrawn, processor stabilizing rods 172 may be deployed, e.g., that expand radially outwardly from the processor 170 to help position the processor 170 within the left atrial appendage 92.

Figure 19A:
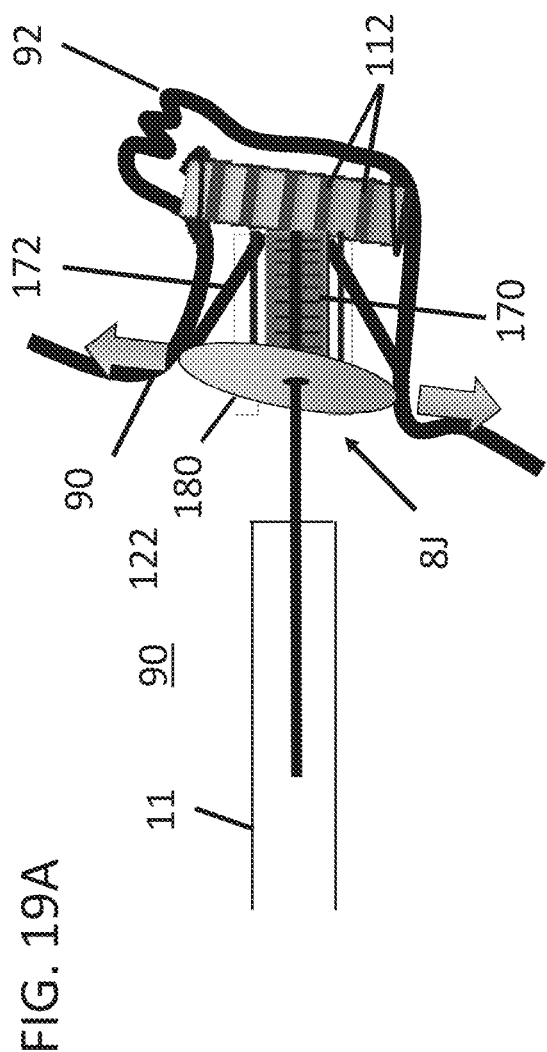

Now moving to FIG. 19A, as the delivery sheath 11 is further withdrawn, the compression portion 180 is released, e.g., by plunger 140, which may cause the compression portion 180 to resiliently expand to at least partially seal the ostium 91 of the LAA 92. The compression portion 180 is designed to deliver radial force against tissue within the left atrial appendage 92 to electrically isolate the left atrial appendage 92. The spiraling member electrodes 112 may be used to verify electrical isolation. These signals may be sent via the processor 170 through wireless connection or coupled through the plunger 140. The processor 170 may also be charged wirelessly from outside the body, e.g., using an inductive charging system (not shown). In some circumstances, electrodes (not shown) may be attached to or otherwise provided on the compression portion 180, e.g., configured to deliver energy to electrically isolate the left atrial appendage 92, e.g., if compression alone does not isolate the left atrial appendage 92.

Figure 19B:
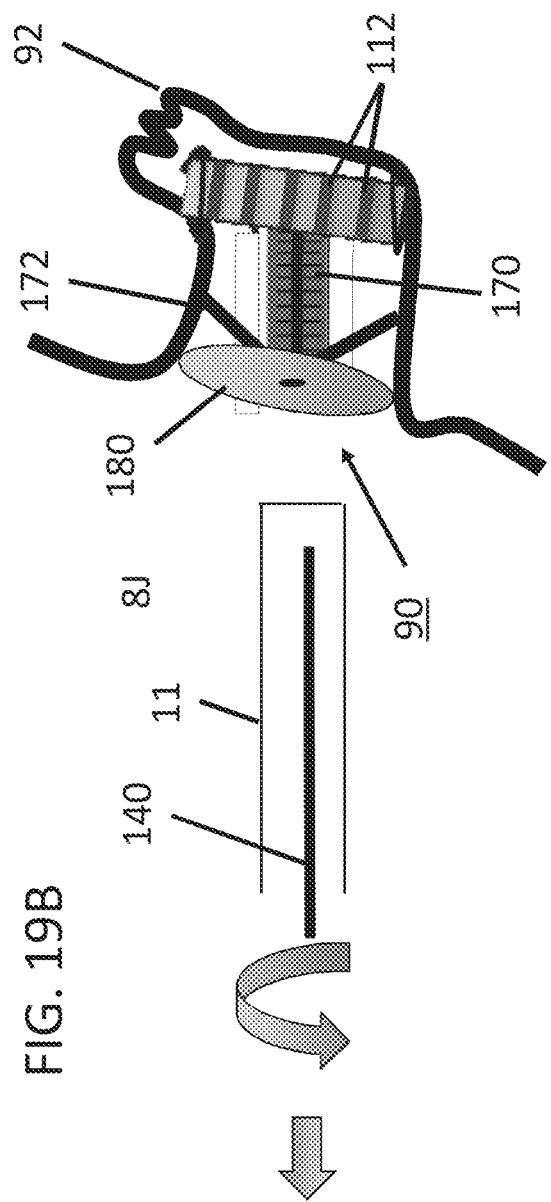

Moving on to FIG. 19B, the plunger 140 may be rotated or otherwise decoupled to free the plunger 140 from the rest of the device. The delivery sheath 11 and plunger 140 may then be removed from the body. As can be seen in this figure, sometimes the processor stabilizing rods 172 are oriented in a different way to optimally position the device within the left atrial appendage 92.

Optionally, the processor 170 may continue to measure one or more patient characteristics based on electrical signals from the electrodes 112, e.g., to identify heart rate, recurrence of atrial fibrillation, or other arrhythmias. The electrodes 112 (or other electrodes) on the device 8J may measure both local electrical signals to identify electrical activity of the left atrial appendage 92 as well as far-field signals of the left atrium and ventricular activation. By measuring the interval between the ventricular signals, the device 8J may identify atrial fibrillation. The processor 170 may send these signals to devices outside of the body for medical intervention.

In another embodiment, the device 8J may identify if local electrical reconnection has occurred within the left atrial appendage 92. In yet another embodiment, the device 8J may measure left atrial pressure, oxygen saturation, cardiac output, and patient activity. In addition or alternatively, an accelerometer may be included on the device 8J, and the device 8J may measure heart rate and patient movement to determine if the heart rate is congruent with patient activity.

Turning to FIGS. 20-21, another exemplary embodiment of the device 8K is shown that includes a plurality of repeating subunits 301-311 connected sequentially to one another by connectors 301c-311c. Although, the device 8K includes eleven subunits 301-311, it will be appreciated that the device 8K may include any desired number of subunits. As shown, the subunits include a first subset that include battery subunits to provide a battery 117 for the device 8K, e.g., the distal two repeating subunits 301-302, as shown in FIG. 20. The connectors 301c-311c connecting the subunits 301-311 may be flexible to allow the subunits 301-311 to move in a desired manner, e.g., during advancement through the delivery sheath 11, yet bias the device 8K to adopt a desired shape when deployed. For example, the connectors 301c-311c may provide hinge points that permit the subunits 301-311 to fold on themselves to provide a desired expanded configuration. Optionally, the connectors 301c-311c may include one or more tines (not shown), electrodes (not shown), or other components to facilitate deployment, e.g., similar to other embodiments described elsewhere herein.

Turning to FIGS. 21A-21B, an exemplary method is shown for deploying the device 8K when the device 8K is advanced out of the delivery sheath 11. Initially, as shown in FIG. 21A, the distal subunit 301 is deployed from the delivery sheath 11, whereupon the connector 301c provides a hinge point, e.g., biased to cause the distal subunit 301 to have an orientation change to the adjacent subunit 302. For example, the connector 301c may be biased to a "U" or other shape, e.g., to cause the distal subunit 301 to rotate or otherwise translate one hundred eighty degrees relative to the second subunit 302. Moving onto FIG. 21B, as the device 8K is further advanced out of the delivery sheath 11, the subunits 302-311 are deployed sequentially, and automatically fold relative to the adjacent subunits into a designed orientation. In some embodiments, the connectors 302c-311c of the device 8K are configured to automatically orient the subunits 302-311 as the device 8K emerges from the delivery sheath 11.

In other embodiments, an external force may be used to force the change in orientation. For example, the connectors 301c-311c may have a hinge type joint where the degrees of freedom are designed to fold the device 8K into the predesigned orientation.

Figure 22:
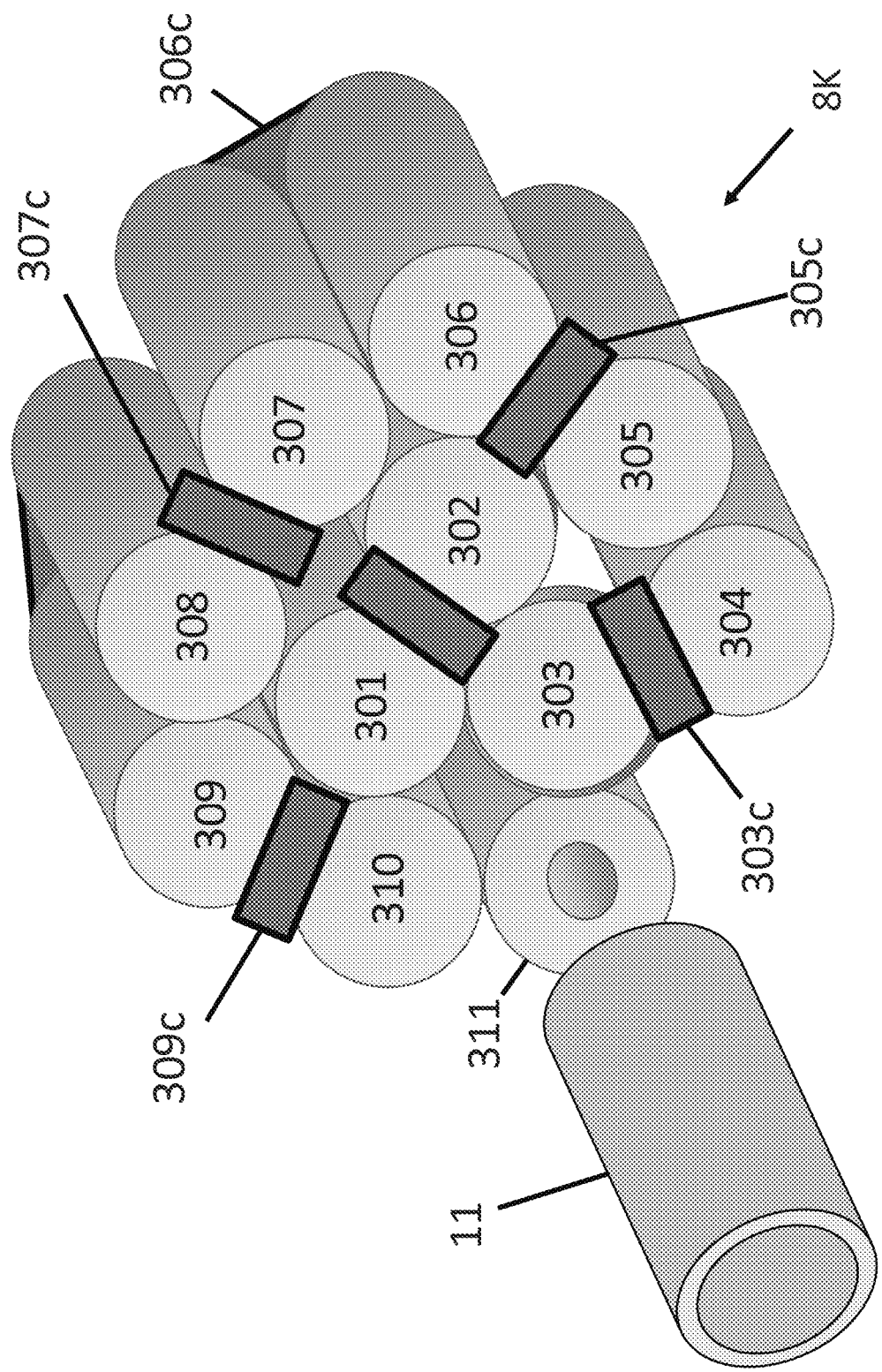

FIG. 22 demonstrates an exemplary expanded configuration where the subunits 301-311 orient themselves into a structure depicted, e.g., where the subunits 301-311 are aligned axially adjacent one another with the connectors 301c-311c alternating between opposite ends of the expanded structure. In this embodiment, the subunits 301-311 are relatively fixed; while the connectors 301c-311c enable the device 8K to fold into the depicted structure.

Figure 23:
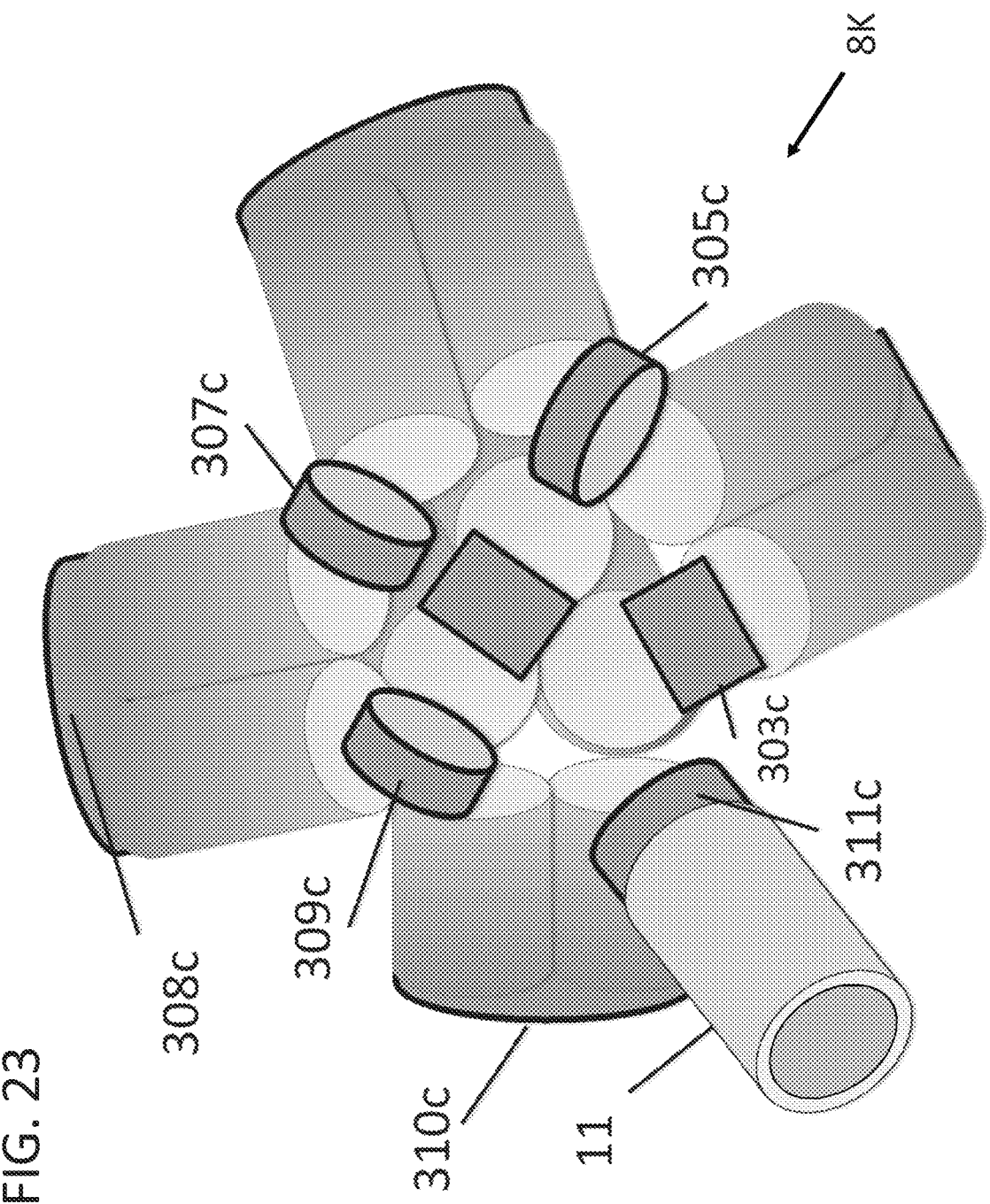

FIG. 23 demonstrates another exemplary expanded configuration of the device 8K where the subunits 301-311 extend radially outwardly from a central region, to provide a conformational change once positioned inside the LAA (not figured). In this example, the connectors 303c, 305c, 307c, 309c, and 311c are designed to expand along their hinge joint, while other connectors 301c, 302c, 304c, 306c, 308c, and 310c are designed to maintain a closed position.

Optionally, one or more tines and/or leads (not shown) may be provided on the connectors 304c, 306c, 308c, and 310c that make contact against the LAA (not shown), e.g., to prevent embolization or to confirm contact through electrical signals, similar to other embodiments herein. In other embodiments, the connectors 304c, 306c, 308c, and 310c may include electrodes (not shown) that may be used for visualization, cardiac pacing, tissue heating (for tissue 'sticking'), ablating, and/or electroporation, as previously described elsewhere herein.

Alternatively, the example shown in FIG. 23 may represent the configuration of the device 8K wherein initially deployed within the left atrium, e.g., when fully deployed from the sheath 11. Features such as tines, hooks, loops, or the like (not shown) on the distal portion of the connectors 304c, 306c, 308c, 310c may be manipulated to narrow the device profile to the configuration presented in FIG. 22 for advancement into the LAA 92.

Figure 24:
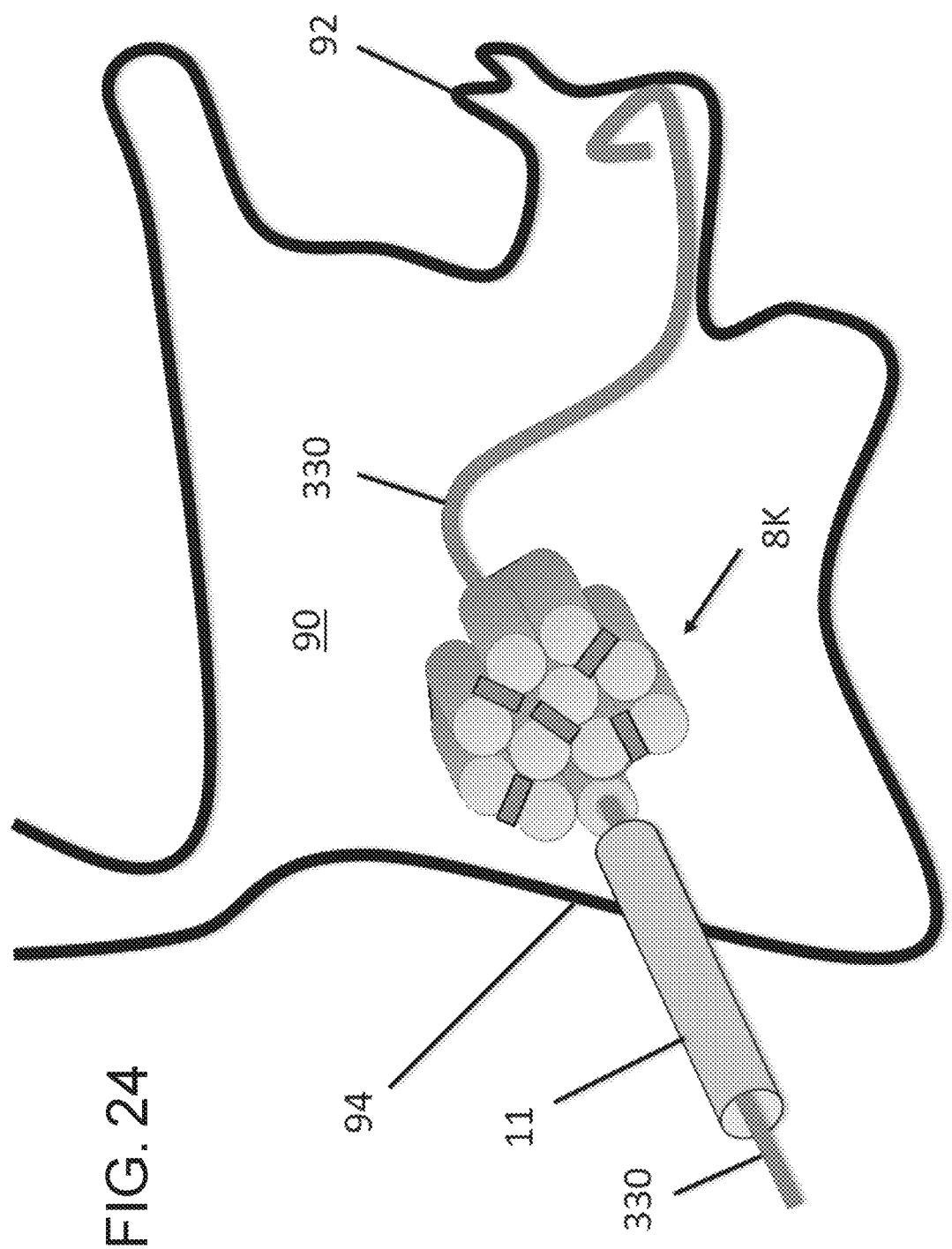

For example, with reference to FIG. 24, the device 8K may be deployed within the left atrium 90 in the configuration shown in FIG. 23 and then folded or otherwise constrained into the configuration shown in FIG. 22, whereupon the folded device 8K may be advanced into the LAA 92, e.g., over guide 330. In this embodiment, the delivery sheath 11 has been advanced into the left atrium 90 through the interatrial septum 94. Once inside the left atrium 90, the elongate device 8G may be advanced to create the desired shape within the left atrium 90, e.g., the deployed configuration shown in FIG. 23. Similar to a ship-in-a-bottle, the device 8K may be manipulated to take on a conformational change within the left atrium 90 to take on a desired shape or structure, e.g., that shown in FIGS. 22 and 24. The conformed device 8K may then be advanced into the LAA 92. Once inside the LAA 92, the device 8K may take on a second conformational change to deploy the device 8K into the LAA 92, e.g., by releasing the device 8K to allow the subunits to resiliently return towards the configuration shown in FIG. 23. The second conformational change locks the device 8G in place within the LAA 92.

In the embodiment depicted in FIG. 24, an elongate guide member 330 is provided that is configured to pass through a delivery lumen of the delivery sheath 11, the proximal connector 311c (not shown), and the proximal subunit 311. In exemplary embodiments, the elongate guide member 330 may be a wire or may be a steerable catheter. In other embodiments, the elongate guide member 330 may be similar to a pigtail catheter with an inner lumen that allows an inner wire to advance through the elongate guide member 330. For example, a distal portion of the elongate guide member 330 may be exposed from the sheath 11 and advanced or otherwise directed into the LAA 92, and then the device 8K may be advanced over the elongate guide member 330 in order to position the device 8K optimally within the LAA 92. In some embodiments, the elongate guide member 330 passes through an inner lumen of the connector 311c and subunit 311 or connector 301c.

In some embodiments, at least the distal portion of the elongate guide member 330 may have a substantially square or other non-circular cross-section. By being square, the elongate guide 330 may be spun to deliver force to the device 8G. For example, if the elongate guide member 330 and an inner lumen of the subunit 311 have a similar cross-section, rotating the elongate guide member 330 about its longitudinal axis may be used to spin the subunit 311. This spinning motion may be designed to expand the device 8K into a desired expanded configuration, for example, the configuration shown in FIG. 23.

In other embodiments, the elongate guide member 330 may include a balloon or other expanded member on the distal portion that may be inflated or otherwise expanded to expand or otherwise deploy the device 8K once in place in the LAA 92. The balloon portion may be asymmetric in order to expand the distal or proximal connectors. In other embodiments, the elongate guide member 330 may also include docking features (not pictured) to interface with the distal portion of the device 8K, e.g., providing an additional landmark for visibility during device placement.

Alternatively, other mechanisms may be provided to orient the device 8K, e.g., including one or more of springs, ratchets, Nitinol or other elastic material, temperature-activated materials, and/or through electricity. As an example, FIG. 33 shows the device 8K in the delivery configuration, with the articulating members of the device 8K including springs and micro-ratchets. Deployment of the FIG. 33 device into the atrium, advancement into the LAA, and further expansion in the LAA are shown in FIGS. 34A-C, respectively. In some embodiments, one of the connectors used to orient the device 8K may also serve as an atraumatic lead in the tip of the delivery sheath 11.

Figure 35B:
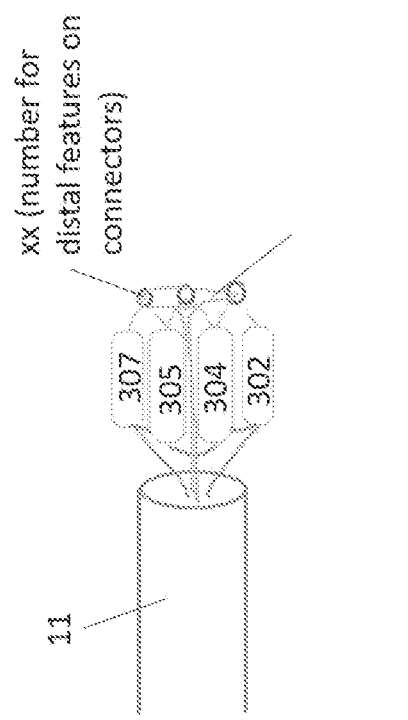
FIGS. 35A and 35B are side views of yet another example a leadless pacemaker device in expanded and contracted conditions, respectively.
Figure 35A:
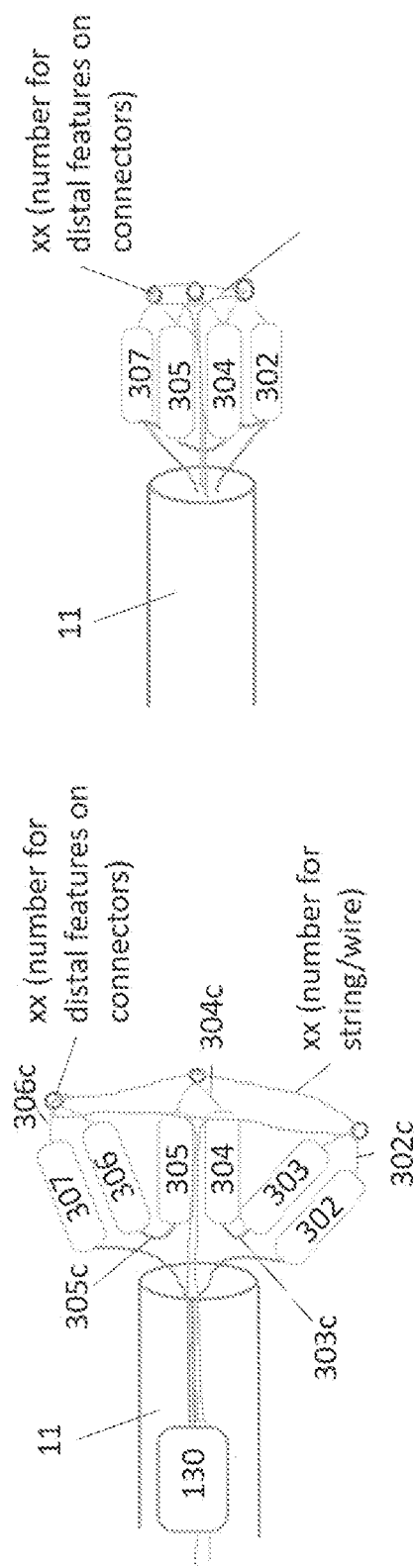
Figure 36D:
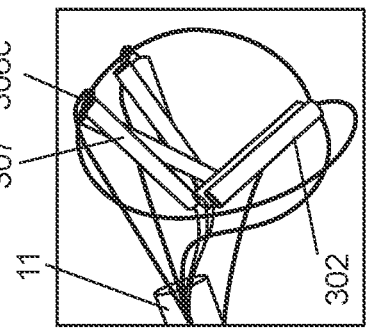
FIGS. 36A-36D are side views of yet another example a leadless pacemaker device being manipulated between expanded and contracted conditions.
Figure 36C:
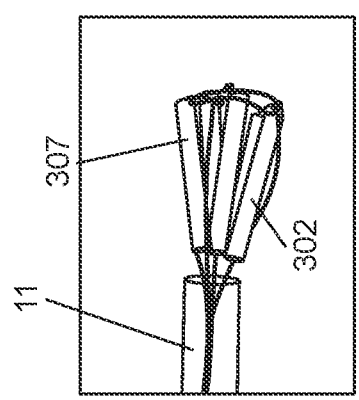
Figure 36B:
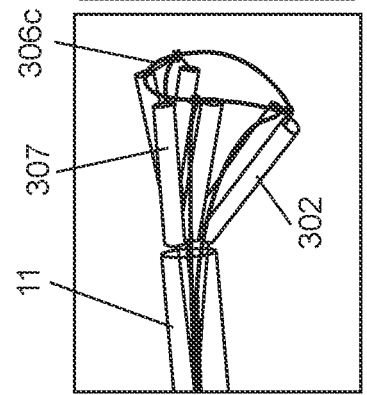
Figure 36A:
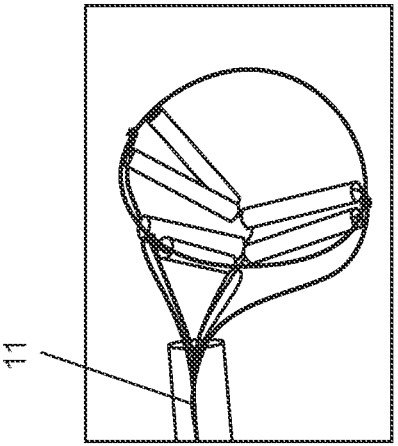

In other embodiments, a string or wire may run through the device 8K, e.g., as shown in FIG. 35A where the device has been deployed in the left atrium. As shown in FIG. 35B, the string may be pulled or otherwise actuated from outside the patient, e.g., using an actuator on the proximal end (not shown) of the sheath 11, to force the subunits to collapse as or after the device 8K is advanced out of the delivery sheath 11. Once the device 8G is positioned within the LAA 92, the string may be relaxed. The relaxation may then cause certain connectors (or all the connectors) to elongate in prescribed directions and/or force to lock the device 8K within the LAA 92. For example, once the string is relaxed, the device 8K may expand automatically through a variety of methods, including but not limited to a spring mechanism, Nitinol, temperature-activated materials, and/or electrical energy. Optionally, the string may be tightened to collapse the device 8K in a desired manner, e.g., into the configuration as illustrated in FIG. 22. As exemplified in FIGS. 36A-36D, repositioning within the LAA 92 while in the narrowed configuration of FIG. 22 may be repeated as needed, by relaxing the string to expand the device 8G (FIG. 36A), verifying the position, and tightening the string to reposition as necessary (FIGS. 36 B-C). After the string is relaxed and placement within the LAA 92 is confirmed (FIG. 36D), the string may then be cut or otherwise separated and withdrawn from the device 8K to leave the device 8K in place within the LAA 92.

In another embodiment, e.g., as illustrated in FIG. 30A, a balloon may be provided on a distal tip (not shown) of the elongate guide member 330, which may be filled with saline and/or other inflation media to expand the subunits 301-311 of the device 8K in a desired manner, e.g., opening the proximal connectors to assume the shape in FIG. 23, creating contact with the distal portion of the device 8K and the LAA 92. As shown in FIG. 30B, if the device 8K needs to be advanced into the LAA 92, the balloon may be inflated within the proximal connectors, thereby expanding the proximal profile of the device 8K and narrowing the position of the distal connectors. The balloon may then be collapsed, the device 8K advanced further into the LAA 92, and the balloon inflated within the distal connectors, e.g., as shown in FIG. 30C. In another embodiment, features on the distal connectors remain captured by the delivery system using a string method similar to that described above, and are leveraged to collapse the device after balloon expansion.

In another embodiment, the delivery sheath 11 may be used to collapse the device 8K in a desired manner, e.g., as shown in FIGS. 31A-31D. In this embodiment, the distal tip 11b of the delivery sheath 11 may include a plurality of axial slots 11c and one or more circumferential strings, wires, or other filaments 11d coupled to the subunits 301-311. The filament(s) 11d may be relaxed to widen the sheath distal diameter, e.g., as shown in FIG. 31B, and then the sheath 11 is advanced over the proximal connectors, as shown in FIG. 13C. Once the proximal connectors and part of the rigid subunits are captured, the circumferential filament 11d may be tightened to collapse the distal tip 11c of the sheath 11 and narrow the device profile, as shown in FIG. 31D, for introduction into the LAA (not shown).

Figure 25A:
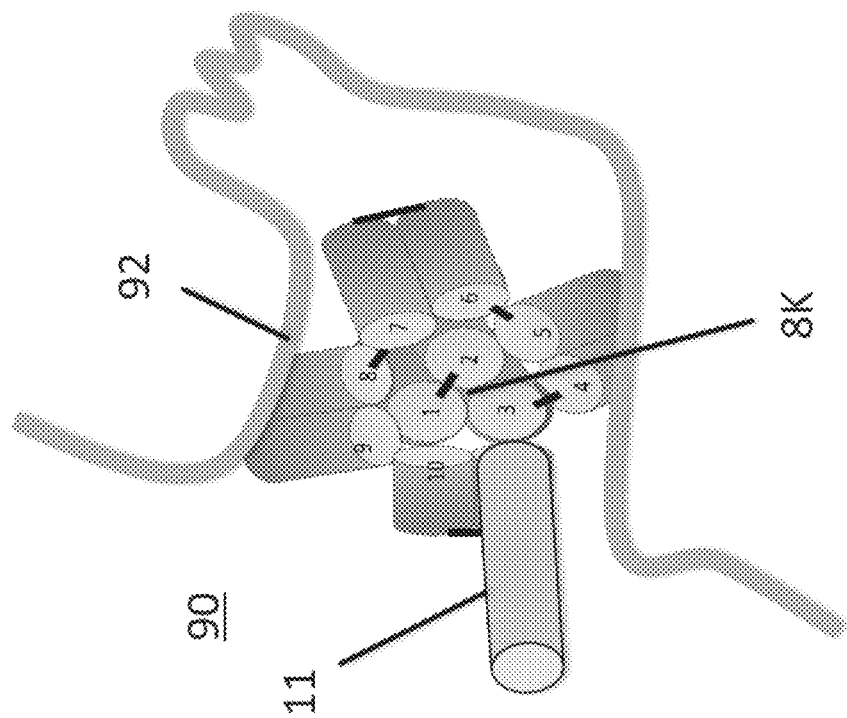
Figure 25B:
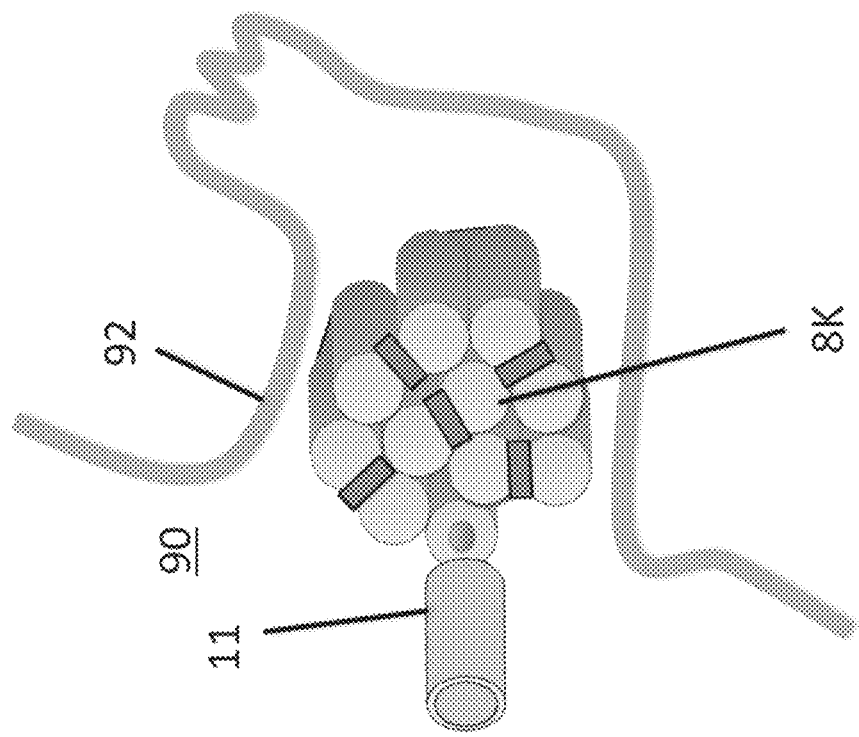

Turning to FIGS. 25A and 25B, an exemplary method is for implanting the device 8K, i.e., deploying, introducing and anchoring the device 8K within the LAA 92. Initially, the device 8K8G is advanced into the LAA 92 in a constrained condition, e.g., similar to the configuration shown in FIG. 22. Moving onto FIG. 25B, the device 8k may then be enlarged or otherwise deployed to connect within the walls of the LAA 92, e.g., similar to the configuration shown in FIG. 23. The device 8K may then undergo tug testing from outside the patient's body to make sure the device 8K is adequately fixed within the LAA 92, visually assessed using fluoroscopy, echocardiography, or other visual mapping methods to confirm device 8G shape and depth of position, and/or contact with the LAA may be confirmed by electrical signal. If needed, the device may be recaptured, repositioned, and then re-deployed, e.g., using any of the methods described elsewhere herein. In another embodiment, if fixation is insufficient, the proximal hinges may be further elongated or otherwise manipulated in order to widen the angle between the rigid subunits, providing greater apposition to the LAA 92.

Figure 26:
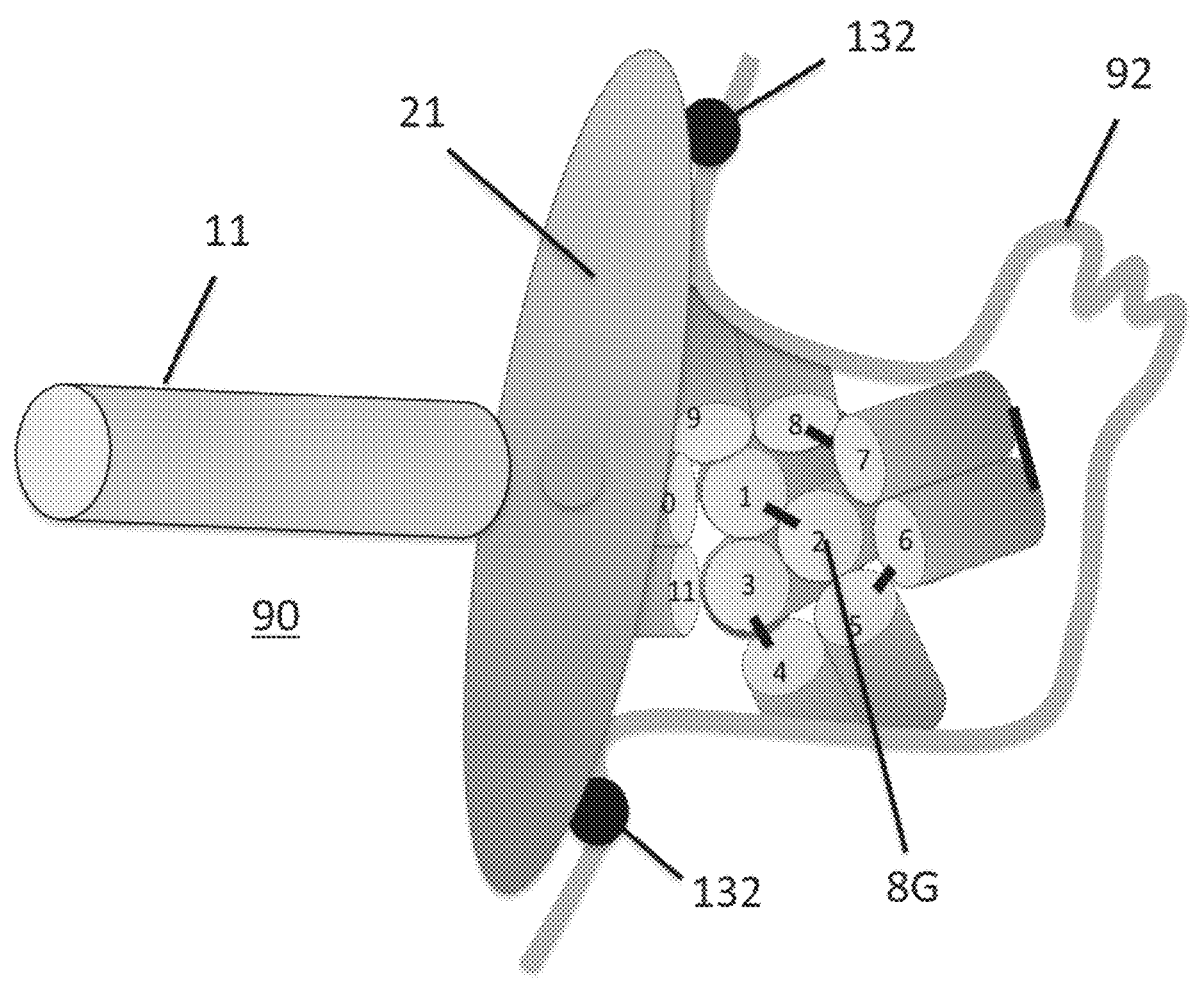

Moving on to FIG. 26, once the device 8K is satisfactorily deployed within the LAA 92, a cover or occluding portion 21 may be deployed to cover the ostium of the LAA 92. The cover 21 may be made out of a variety of materials. The cover 21, which may be similar to cover 130 or any of the other embodiments described elsewhere herein, is designed to cap the ostium of the LAA 92 and prevent thrombus or clot that may form within the LAA 92 from leaving the LAA 92. In some embodiments, the cover 21 includes one or more pacing electrodes 132, e.g., located on the LAA 92 side of the cover 21. These pacing electrodes 132 may be configured to contact the wall of left atrium 90 outside of the LAA 92. Therefore, if the LAA 92 is electrically isolated, the pacing electrodes 132 are still able to sense and capture atrial tissue. The pacing electrodes 132 may be single or bipolar electrodes. The pacing electrodes 132 are therefore able to sense atrial depolarizations and deliver pacing stimulations to pace the atrial tissue. In some embodiments, atrial anti-tachycardia pacing (ATP) may be delivered from one electrode 132 and sensed by other electrodes. Therefore, pacing stimulations may be delivered at one location; and distant electrodes are able to determine if the pacing stimulations are capturing heart tissue. The ATP algorithm may then change pacing strategies based on whether the pacing stimulations are capturing the atria.

In some embodiments, the center of the cover 21 is deployed first, followed by the outer circumference of the cover 21. In other embodiments, the outer circumference is deployed first, contact with ostium verified through methods described above, and the remainder of the cover 21 deployed. If the leads in the cover 21 are unable to obtain sufficient contact with the ostium, the cover 21 may be recovered into the delivery system, repositioned, and redeployed.

Figure 32B:
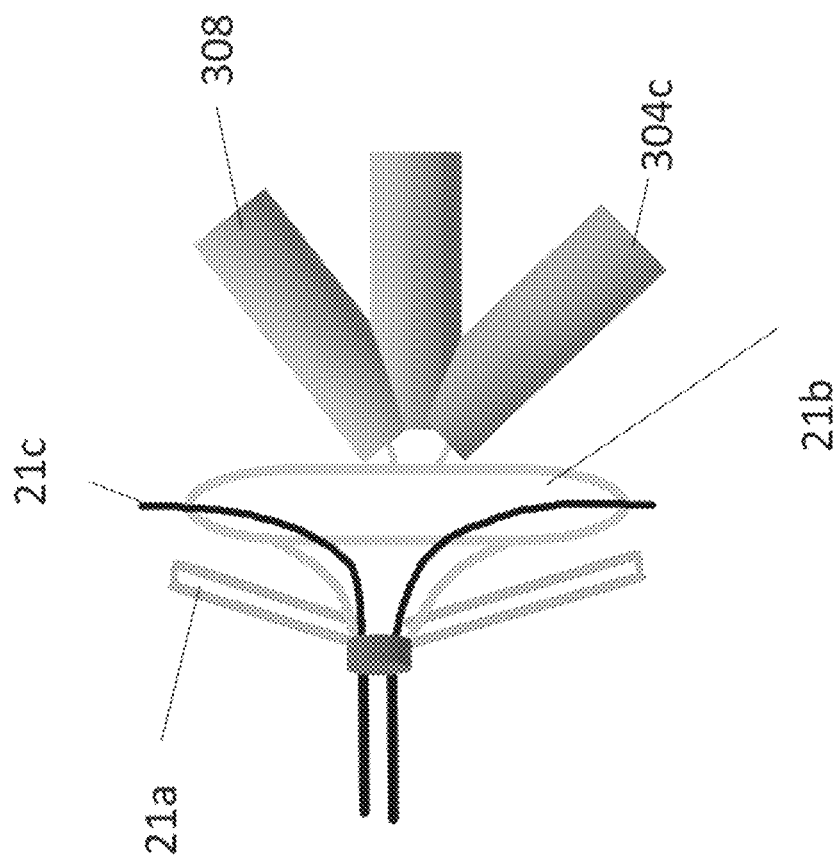
FIGS. 32A and 32B are side views of another exemplary embodiment of a leadless pacemaker device.
Figure 32A:
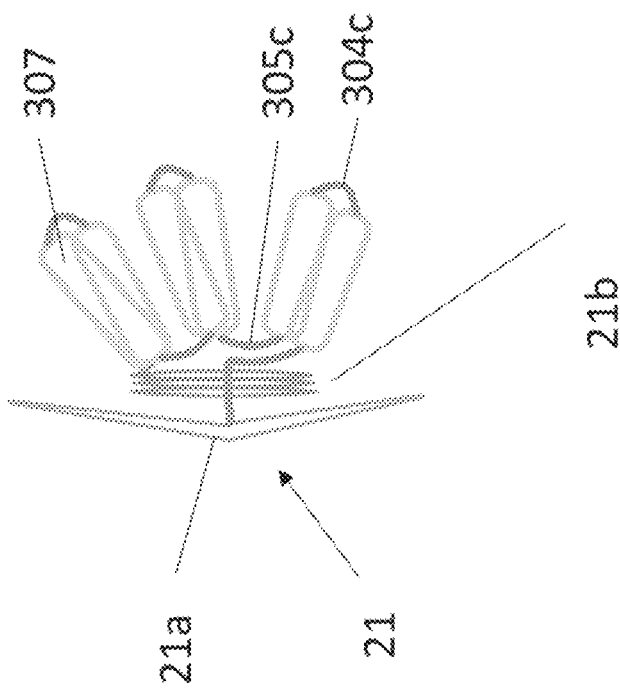

Turning to FIGS. 32A and 32B, in other embodiments, the cover 21 may include two regions, a first region 21a that caps the ostium of the LAA and a middle member 21b that sits within the LAA. In some embodiments, the middle member 21b may include one or more temporary or permanent leads 21c for electrical isolation of the LAA, e.g., as shown in FIG. 32B. The middle member 21b may be deployed before the cap 21a to allow for electrical isolation treatments to be conducted before the cap 21a is deployed. In some embodiments, the cover 21 and middle member 21b may include one or more channels through which the leads 21c used for electrical isolation or materials for electroporation may be advanced and removed. In other embodiments, the middle member 21b itself may be composed of materials that may be utilize to complete established isolation methods. Furthermore, in some embodiments, the middle member 21b provides tension between the cover 21a and the remainder of the device 8K implanted further in the LAA, ensuring apposition between the cover 21a and the ostium of the LAA 92. In other embodiments, the deployment of the cover 21a or middle member 21b further widens the angle between the rigid subunits in the distal portion of the device 8K.

Figure 27B:
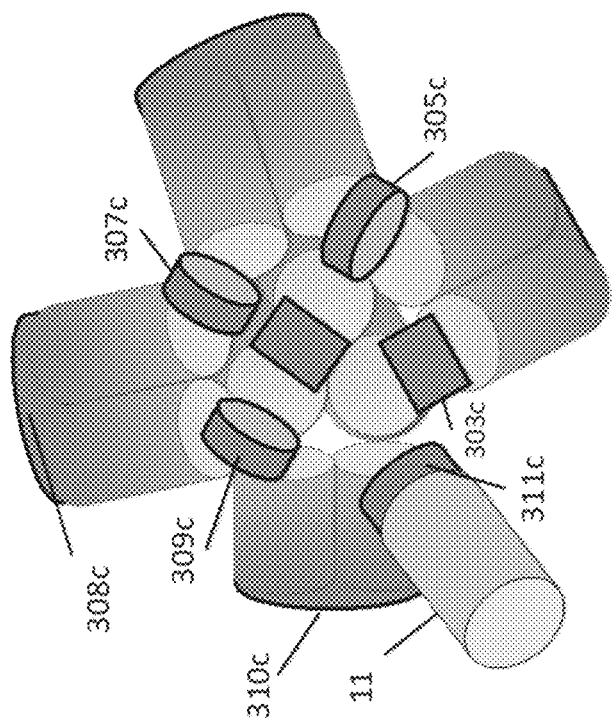
FIGS. 27A-27B show other exemplary embodiments of a leadless pacemaker designed for deployment within the left atrial appendage.
Figure 27A:
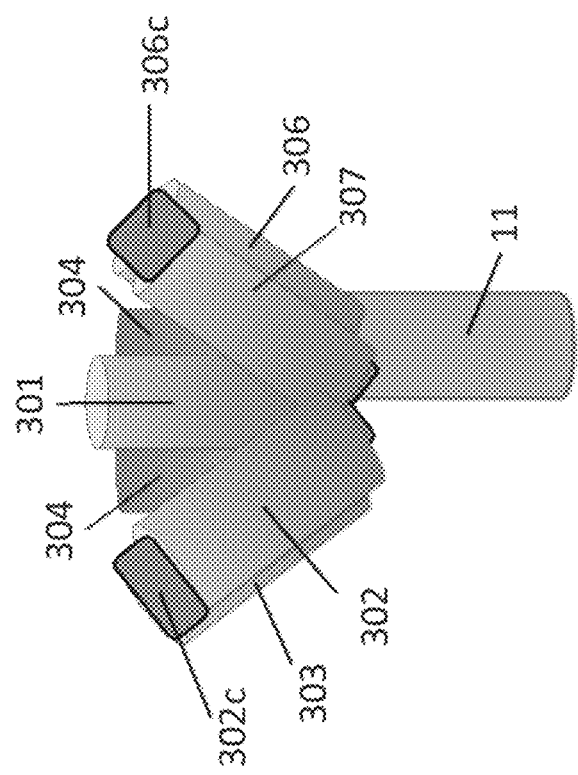

Turning to FIGS. 27A and 27B, two different expanding devices are shown that include a different number of subunits. FIG. 27A shows a device with seven (7) subunits 301-307, while FIG. 27B shows a device with eleven (11) subunits 301-311. In either embodiment (or any of the others wherein), the device may include two or more subunits that provide a housing to contain the various components previously described, e.g., a processor, battery, communications interface, and the like. The subunits may take on various lengths and sizes. For example, in the embodiments shown in FIG. 21-FIG. 26, the subunits may have lengths longer than about ten millimeters (10 mm) and less than about thirty millimeters (30 mm). The diameter of the subunits may be larger than about three millimeters (3 mm) and less than about six millimeters (6 mm). In some embodiments, the subunits are sized to be about twenty one millimeters (21 mm) in length (+/−5 mm) and about four millimeters (4 mm) in diameter (+/−1 mm).

Figure 28:
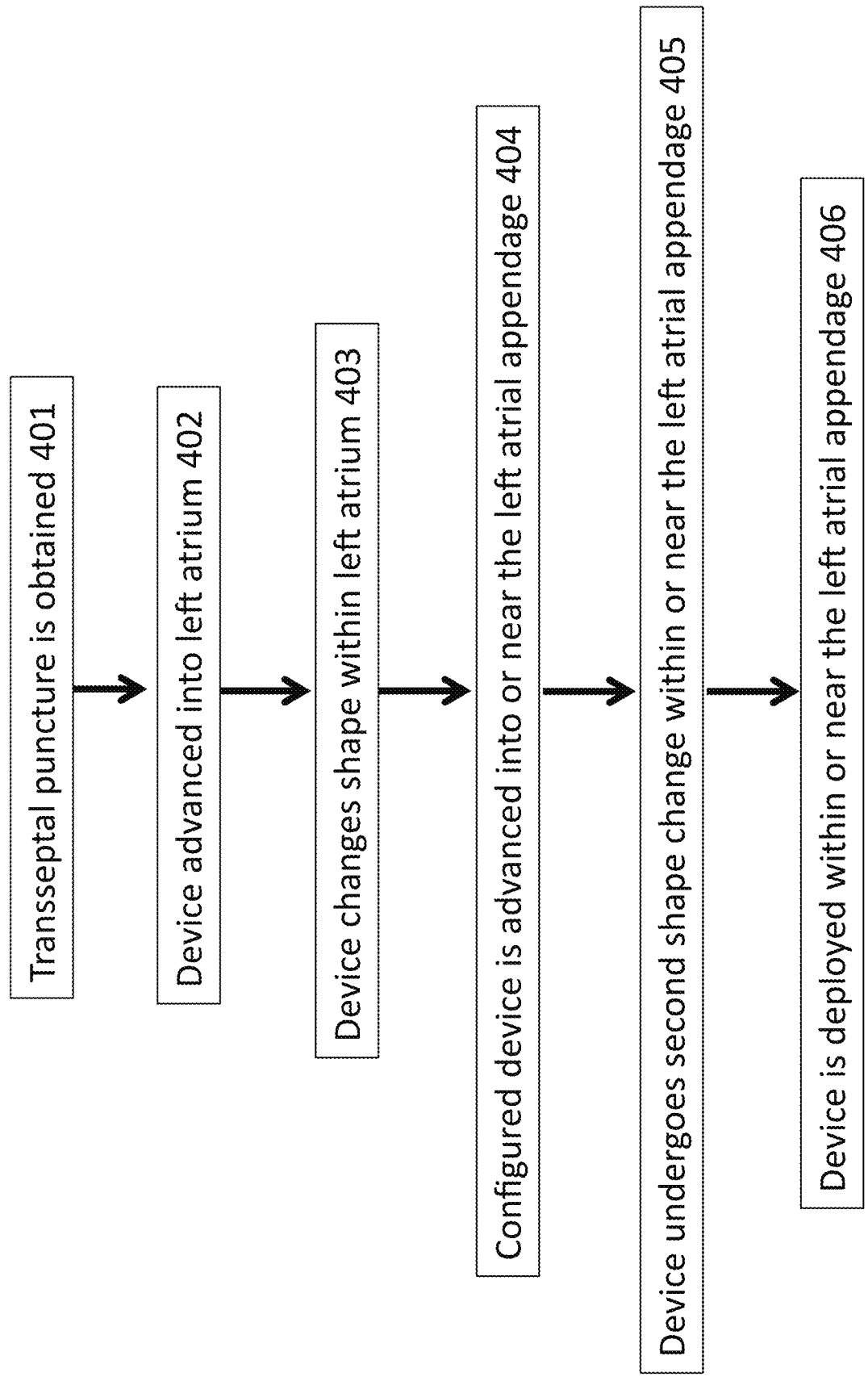
FIG. 28 is a flow diagram of an exemplary method for deploying a leadless pacemaker device.

Turning to FIG. 28, a flow diagram is shown illustrating an exemplary method for implanting a device, such as the device 8K (or any other devices herein). In step 401, access of the left atrium is obtained. A delivery sheath is typically placed across from the right atrium into the left atrium. In step 402, the device is advanced into the left atrium. Moving to step 403, once part of the device is located within the left atrium, and the device changes shape (e.g., automatically upon deployment or upon being actuated). The shape change may be described as a conformation change or a configuration change. Moving to step 404, the conformed or configured device may then be advanced into or near the left atrial appendage. In step 405, the device may then undergo a second shape change within or near the left atrial appendage (e.g., constrained or otherwise manipulated into a smaller profile). This second shape change may also be described as a second conformational or second configuration change. In some embodiments, this second shape change is utilized to keep the device within or near the left atrial appendage. In step 406, the device may then be deployed within or near the left atrial appendage. The delivery tools may then be removed from the left atrium.

Figure 29:
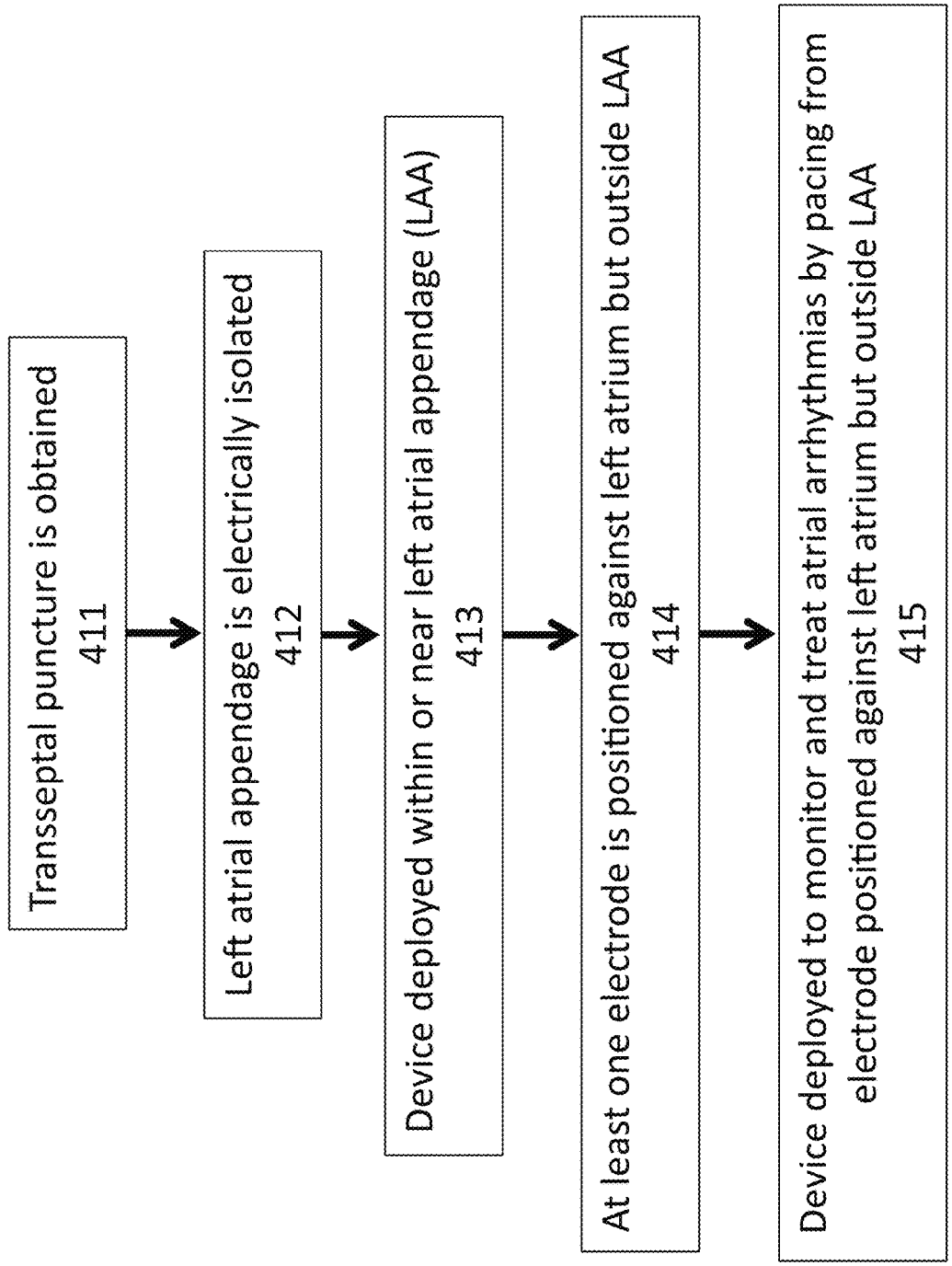
FIG. 29 is a flow diagram of another exemplary method for deploying a leadless pacemaker device.

FIG. 29 is another flow diagram describing another exemplary embodiment implanting any of the devices described herein. In step 411, trans-septal puncture is obtained. In step 412, the left atrial appendage is electrically isolated. Electrical isolation may be achieved through heating, freezing, laser energy, or electroporation. Electrical isolation may be achieved through an ablation catheter that is separate from the device that will be deployed within or near the left atrial appendage. Therefore, in one embodiment, an ablation catheter may be used to electrical isolate the left atrial appendage. After the left atrial appendage is electrically isolated, we move to step 413 where the device is deployed within or near the left atrial appendage. In other embodiments, the device that will be deployed into or near the left atrial appendage achieves electrical isolation. Moving to step 414, at least one electrode is positioned against the left atrium but outside the left atrial appendage. In step 415, the device is deployed to monitor and treat atrial arrhythmias by pacing from the electrode positioned against the left atrium but outside the left atrial appendage. In some embodiments, the device has at least two electrodes spaced apart from each other against left atrial tissue but outside the left atrial appendage. By having two electrodes spaced apart, one electrode can delivery anti-tachycardia pacing (ATP) while the second electrode can monitor for local electrical activity to determine if the ATP pacing pulses are capturing at least a section of atrial tissue.

In another embodiment, an electrode is placed deep into the left atrial appendage. This electrode may be used to sense electrical activity. For example, ventricular activity may be determined. In another embodiment, high output pacing from an electrode positioned near the left ventricle can be used to pace the left ventricle. The device may deliver high-powered shocks or defibrillations to convert both atrial and ventricular arrhythmias. When delivering atrial cardioversions, these high powered pulses should be synced to ventricular activity.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A leadless pacemaker device for implantation within or near a left atrial appendage extending from a left atrium of a heart to monitor and/or treat a patient with conduction abnormalities and/or cardiac dysrhythmias, the device comprising:
 a battery capable of storing electrical energy;
 at least one electrode capable of sensing and pacing the left atrium;
 a control processor capable of processing data;
 a communication module to communicate outside of the patient;
 a linear chain of subunits coupled together by connectors sized for introduction into the left atrial appendage, wherein the connectors are configured to allow each subunit to change orientation relative to any adjacent subunits; and
a cover portion coupled to the subunits and configured to close the left atrial appendage to prevent thrombus from within the left atrial appendage to embolize out of the left atrial appendage of the left atrium after positioning the subunits within the left atrial appendage.

2. The device of claim 1, wherein the subunits are cylindrical in shape, wherein each of the subunits defines a length that is between about ten and thirty millimeters (10-30 mm), and a diameter that is between about three and six millimeters (3-6 mm).

3. The device of claim 1, further comprising that the at least one electrode capable of sensing and pacing the left atrium is configured to be located against the wall of the left atrium outside of the left atrial appendage and at least two millimeters (2 mm) away from the ostium of the left atrial appendage.

4. The device of claim 1, further comprising at least one electrode configured for delivering ablation energy.

5. The device of claim 1, wherein the subunits are configured to undergo a first conformational change upon entering the left atrium and then undergo a second conformational change after being positioned within the left atrial appendage.

6. The system of claim 1, wherein each of the subunits is rigid and wherein the connectors allow the subunits to rotate or translate relative to adjacent subunits.

7. The system of claim 6, wherein each of the rigid subunits has a fixed length between opposite ends, and wherein the connectors are coupled to the opposite ends of a plurality of the rigid subunits.

8. The system of claim 1, wherein the connectors are more flexible than the subunits.

9. An elongate implantable pacemaker system for implantation within or near a left atrial appendage extending from a left atrium of a heart to monitor and/or treat a patient with conduction abnormalities and/or cardiac dysrhythmias, the system comprising;
a housing having a proximal end and a distal end, the housing sized for implantation within a left atrial appendage of a heart, the housing comprising a linear chain of subunits coupled together by connectors sized for introduction into the left atrial appendage;
a battery and a processor carried by the housing;
an expandable cover operatively coupled with the housing and configured to close the left atrial appendage after positioning the housing within the left atrial appendage; and
at least one pacing electrode,
wherein the connectors allow the subunits to rotate or translate relative to adjacent subunits such that the housing is configured to undergo a configuration change within a left atrium of the heart before being advanced into the left atrial appendage, and
wherein the cover is adapted to prevent blood clots from leaving the left atrial appendage after positioning the housing within the left atrial appendage.

10. The system of claim 9, wherein the at least one pacing electrode is configured to be placed against a wall of the left atrium but outside the left atrial appendage.

11. The system of claim 9, wherein the processor is coupled to the at least one pacing electrode and is configured to monitor signals from the heart to identify cardiac arrhythmias and to deliver anti-tachycardia pacing pulses via the at least one pacing electrode to the wall of the left atrium to treat abnormal fast atrial arrhythmias.

12. The system of claim 10, wherein the processor is further configured to monitor for slow atrial rates in the heart and deliver one or more pacing pulses to speed up the atrial rates.

13. The system of claim 9, wherein the processor is configured to deliver high output pacing from or near the left atrial appendage in order to capture ventricular tissue in order to speed up the ventricular rate.

14. The system of claim 9, wherein the cover is configured to be aligned by at least one electrode configured to deliver electroporation energy to ablate atrial tissue capable of delivering ablation energy to electrically isolate the left atrial appendage from the rest of the left atrium.

15. The system of claim 9, wherein the housing is configured to undergo the configuration change by one or more connectors coupled to the housing or by a delivery system.

16. A leadless pacemaker system for implantation within or near a left atrial appendage extending from a left atrium of a heart to monitor and/or treat a patient with conduction abnormalities and/or cardiac dysrhythmias, the system comprising:
a delivery sheath comprising a proximal end, a distal end sized for introduction into a left atrium of a heart, and a lumen extending between the proximal and distal ends;
a pacemaker device comprising a plurality of substantially rigid elements deployable sequentially through the lumen from the distal end into the left atrium, each element having a length between about ten and thirty millimeters (10-30 mm), the elements configured to adopt an expanded configuration within the left atrium;
an actuator for advancing the elements from the left atrium into the left atrial appendage, and releasing the elements to implant the device within the left atrial appendage; and
a cover operatively coupled to the elements and slidably received within the lumen such that the cover is deployed from the lumen after deploying the elements, the cover expandable for isolating the left atrial appendage from the left atrium after advancing the elements into the left atrial appendage.

17. The system of claim 16, wherein the elements are connected sequentially together by connectors between adjacent elements, the connectors biased to a nonlinear shape such that, when the elements are deployed from the distal end of the delivery sheath, the connectors automatically cause the elements to spiral or fold into the expanded configuration.

18. The system of claim 17, further comprising a constraining mechanism for constraining the elements in a contracted configuration having a lower profile than the expanded configuration before advancing the elements into the left atrial appendage.

19. The system of claim 18, wherein the actuator is configured to release the elements from the contracted configuration once advanced into the left atrial appendage such that the connectors bias the elements back towards the expanded configuration to secure the elements within the left atrial appendage.

20. The system of claim 16, wherein the elements are connected sequentially together by connectors between adjacent elements, and wherein the actuator is coupled to the connectors to direct the connectors to a nonlinear shape and cause the elements to spiral or fold into the expanded configuration.

21. The system of claim 20, further comprising a constraining mechanism for constraining the elements in a contracted configuration having a lower profile than the expanded configuration before advancing the elements into the left atrial appendage.

22. The system of claim 16, further comprising one or more electrodes carried by the cover, the one or more electrodes configured to contact a wall of the left atrium outside the left atrial appendage when the left atrial appendage is isolated by the cover.

23. The system of claim 22, further comprising a processor coupled to the one or more electrodes configured to:
   identify a cardiac condition of the heart warranting pacing; and
   deliver electrical pacing via at least one of the one or more electrodes until the cardiac condition is remedied.

24. The system of claim 16, wherein the pacemaker device further comprises a plurality of electrodes coupled to a power source, the electrodes configured to deliver energy to ablate atrial tissue to electrically isolate the left atrial appendage from the rest of the left atrium.

25. The system of claim 16, wherein the elements carry one or more electrodes, the system further comprising a power source coupled to the one or more electrodes to deliver energy to heat tissue adjacent tissue to secure the elements within the left atrial appendage.

* * * * *